(12) United States Patent
Surmacz et al.

(10) Patent No.: US 8,470,772 B2
(45) Date of Patent: Jun. 25, 2013

(54) LEPTIN AGONIST AND METHODS OF USE

(75) Inventors: Eva Surmacz, Philadelphia, PA (US); Laszlo Otvos, Jr., Audubon, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 332 days.

(21) Appl. No.: 12/919,408

(22) PCT Filed: Feb. 27, 2009

(86) PCT No.: PCT/US2009/001231
§ 371 (c)(1),
(2), (4) Date: Aug. 25, 2010

(87) PCT Pub. No.: WO2009/108340
PCT Pub. Date: Sep. 3, 2009

(65) Prior Publication Data
US 2011/0015124 A1    Jan. 20, 2011

Related U.S. Application Data

(60) Provisional application No. 61/067,376, filed on Feb. 27, 2008.

(51) Int. Cl.
*A61K 38/22* (2006.01)
*A61K 38/10* (2006.01)
*A61K 38/14* (2006.01)
*A61P 15/08* (2006.01)

(52) U.S. Cl.
USPC ........... 514/5.8; 514/21.5; 514/9.8; 514/20.9; 530/327

(58) Field of Classification Search
None
See application file for complete search history.

(56) References Cited

U.S. PATENT DOCUMENTS

| | | | |
|---|---|---|---|
| 6,777,388 B1 | 8/2004 | Grasso et al. | |
| 7,208,572 B2 | 4/2007 | Grasso et al. | |
| 2005/0288223 A1 | 12/2005 | Lucas et al. | |
| 2006/0003938 A1 | 1/2006 | Otvos .............................. | 514/12 |
| 2006/0099150 A1 | 5/2006 | Houston et al. ................. | 424/46 |

FOREIGN PATENT DOCUMENTS

| WO | WO 01/21647 A2 | | 3/2001 |
|---|---|---|---|
| WO | WO-02/062833 | * | 8/2002 |
| WO | WO 02/062833 A2 | | 8/2002 |
| WO | WO 2004/039832 | | 5/2004 |

OTHER PUBLICATIONS

Witt, 2001, Peptides, 22, 2329-2343.*
Otvos, 2007, Peptide Sciences, 88 (4), Abstract 172, p. 556.*
Lee, 2001, Drugs of the future, 26 (9), p. 873-881.*
Kovalszky, 2010, Diabetes, obesity and metabolism, 12, 393-402.*
Otvos, et al., "Towards lepting-derived peptides in cancer therapy: Partial agonists acting on the leptin—leptin receptor interface", *International Journal of Obesity*, vol. 31, No. Suppl. 1, May 2007.
Egleton, R.D., et al. Improved bioavailability to the brain of glycosylated Met-enkephalin analogs. *Brain Research*, 881, pp. 37-46 (2000).
Chan, J.L., et al. Role of leptin in energy-deprivation states: normal human physiology and clinical implications for hypothalamic amenorrhea and anorexia nervosa. *The Lancet*, 366:9479, pp. 74-85 (2005).
Dhanasekaran, M., et al. New Prospects for Glycopeptide Based Analgesia: Glycoside-Induced Penetration of the Blood-Brain Barrier. *Current Drug Delivery*, 2, pp. 59-73 (2005).
Witt, K.A., et al. Peptide drug modifications to enhance bioavailability and blood-brain barrier permeability. *Peptides*, 22, pp. 2329-2343 (2001).
Authors, Title "Abstracts of 20th American Peptide Society Symposium, Jun. 26-30, Montreal, Canada," *Peptide Sciences* 88(4):556, Abstr. 172, (Jun. 4, 2007).
Niv-Spector, et al., "Identification of the hydrophobic strand in the A-B loop of leptin as major binding site III: implications for large-scale preparation of potent recombinant human and ovine leptin antagonists," *Biochem. J.*, (2005) 391:221-230.
Iserentant, et al., "Mapping of the interface between leptin and the leptin receptor CRH2 domain," *Journal of Cell Science*, 118:2519-2527 (Mar. 16, 2005).
Peelman, et al., "Mapping of the Leptin Binding Sites and Design of a Leptin Antagonist," *The Journal of Biological Chemistry*, vol. 279, No. 39, Issue of Sep. 24, pp. 41038-41046, 2004.
Gonzalez, et al., "A Peptide Derived from the Human Leptin Molecule Is a Potent Inhibitor of the Leptin Receptor Function in Rabbit Endometrial Cells," *Endocrine*, vol. 21, No. 2, pp. 185-195, Jul. 2003.
Knappe, et al., "Drug Development-targeted Screening of Leptin Agonist Glycopeptides," *Int J Pept Res Ther*, 2008, 14:247-254.
Otvos, Jr., et al., "Development of a pharmacologically improved peptide agonist of the leptin receptor," *Biochimica et Biophysica Acta*, 2008 1783:1745-1754.

* cited by examiner

*Primary Examiner* — Satyanarayana R Gudibande
(74) *Attorney, Agent, or Firm* — Drinker Biddle & Reath LLP

(57) ABSTRACT

Peptides are provided having leptin receptor agonist activity. The peptides are useful for treating obesity, insulin resistance, lipodystrophy and hypothalamic amenorrhea, anorexia-related infertility, among other diseases and conditions related to leptin deficiency and/or leptin resistance.

26 Claims, 4 Drawing Sheets

LEPTIN AGONIST AND METHODS OF USE

This application claims the benefit from U.S. Provisional Application No. 61/067,376, filed Feb. 27, 2008, the entire disclosure of which is incorporated herein by reference in its entirety.

FIELD OF THE INVENTION

The invention relates to leptin peptide fragments and their use as agonists of the leptin receptor.

BACKGROUND OF THE INVENTION

Leptin is a neurohormone that acts in the hypothalamus to regulate energy balance and food intake (M. Wauters, et al., *Eur. J. Endocrinol.*, 2000, 143, 293-311). Recessive mutations in the leptin or the gene for its receptor, ObR, result in profound obesity and type II diabetes mellitus (Y. Zhang, et al., *Nature*, 1994, 372, 425-432). In addition to its role as a neurohormone and energy regulator, leptin can modulate several physiological processes, such as fertility, lactation, immune response, bone remodeling, hematopoiesis, and cognitive functions. On a cellular level, leptin can act as a mitogen, survival factor, metabolic regulator, or pro-angiogenic factor (M. Wauters, et al., *Eur. J. Endocrinol.*, 2000, 143, 293-311).

Mature human leptin is secreted as a 146-amino acid protein, with a bundle of 4 helices (helices A-D) with an up-up-down-down topology (F. Zhang, et al., *Nature*, 1997, 387, 206-209). Superimposition of the leptin sequence with other cytokines, such as human IL-6, bovine G-CSF, human oncostatin M, etc., reveals three potential bivalent receptor binding sites (sites mostly around the pairwise helices (F. Peelman et al., *J. Biol. Chem.*, 2004, 279, 41038-41046).

Leptin binds to the extracellular domain of its receptor, ObR, which can be expressed as multiple isoforms. The long isoform of ObR (ObR1) can induce multiple intracellular signaling pathways, for instance, the classic cytokine JAK2/STAT3 (Janus kinase 2/signal transducer and activator of transcription 3) pathway; the Ras/ERK1/2 (Ras/extracellular signal-regulated kinases 1/2) signaling cascade; and the PI-3K/Akt/GSK3 (phosphoinositide 3 kinase/protein kinase B/glycogen synthase kinase 3) growth/antiapoptotic pathway. In addition, leptin has been found to induce PLC (phospholipase C)-γ, PKC (protein kinase C), p38 kinase, and nitric oxide (NO) production (C. Bjorbaek, et al., *J. Biol. Chem.*, 1997, 272, 32686-32695; G. Sweeney, *Cell. Signal.*, 2002, 14, 655-663; L. Zabeau, et al., *FEBS. Lett.*, 2003, 546, 45-50). Ultimately, induction of ObR1 can activate several genes involved in cell proliferation, including c-fos, c-jun, junB, egr-1, and socs3, and upregulate the expression angiogenic factors, such as VEGF (G. Sweeney, *Cell. Signal.*, 2002, 14, 655-663; L. Zabeau, et al., *FEBS. Lett.*, 2003, 546, 45-50; K. A. Frankenberry, et al., *Am. J. Surg.*, 2004, 188, 560-565).

The receptor binding site around residue 40 of leptin is labeled as site I. The residues at the very N-terminus and in the middle of the protein are labeled as binding site II, and the residues at the C-terminus as binding site III. Interfering with these binding surfaces may increase or decrease the efficiency of leptin/ObR binding and modulate downstream ObR signaling. Full-length leptin and point mutants of full-length leptin have been examined as potential therapeutic agents for obesity. However, results were disappointing, largely due to leptin resistance in obese people as well as difficulties in recombinant leptin delivery to the central nervous system (J. M. Montez, et al., *Proc. Natl. Acad. Sci. USA*, 2005, 102, 2537-2542).

As a first indication of the possibility of growth arrest upon ObR inactivation, the proliferation rate of leptin-sensitive BAF/3 cells stably transfected with the long form of human leptin receptor was measured after treatment of leptin fragments and their mutants (L. Niv-Spector et al., *Biochem. J.*, 2005, 391, 221-230). It was found that single-point mutations in leptin binding site III lower the affinity between the ligand and the receptor, attenuating the agonistic activity and converting those mutants into both partial antagonists and weak agonists.

The multiple roles leptin plays in various biological processes suggest that it is not straightforward to obtain true leptin agonists or antagonists that do not change the downstream signaling effect upon varying environmental conditions. Indeed, the emergence of both partial antagonists and weak agonists as listed above indicates that, depending upon the cell lines used, as well as the presence or absence of native, unmodified leptin, the same mutant protein or large subunit can trigger different biological responses. The use of such proteins and peptides in human or veterinary therapy will therefore likely meet regulatory opposition, as the peptides do not demonstrate pure, controllable agonist activity of the leptin receptor.

What is needed is a leptin-based peptide agonist for use in leptin-deficient diseases such as obesity, lipodystrophy, diet induced food craving and anorexia-related infertility. The present invention addresses and meets these needs.

SUMMARY OF THE INVENTION

Compounds of the invention are useful as ObR agonists.

According to the invention, a compound is provided of formula I:

(I)
X-Glu-Val-Val-Ala-Leu-Y-Arg-Leu-Z   (SEQ ID NO: 14)

wherein:
(a) X is selected from the group consisting of
  (i) zero amino acids,
  (ii) a hydroxyamino acid,
  (iii) a saccharide-modified hydroxyamino acid,
  (iv) $X_1$-$X_2$, wherein $X_1$ is a hydroxyamino acid, a saccharide-modified hydroxyamino acid or Asn, and $X_2$ is a hydroxyamino acid, a saccharide-modified hydroxyamino acid or Asn; and
  (v) $X_3$-$X_4$-$X_5$, wherein $X_3$ is a non-natural amino acid or an acetylated amino acid, $X_4$ is a hydroxyamino acid, a saccharide-modified hydroxyamino acid or Asn, and $X_5$ is a hydroxyamino acid, a saccharide-modified hydroxyamino acid or Asn,
(b) Y is a hydroxyamino acid, a saccharide-modified hydroxyamino acid or Asn, and
(c) Z is selected from the group consisting of
  (i) a non-natural amino acid which resists exopeptidase activity in a mammal, and
  (ii) $Z_1$-$Z_2$, wherein $Z_1$ is a natural or non-natural amino acid, and $Z_2$ is a natural or non-natural amino acid which resists exopeptidase activity in a mammal,
wherein the C-terminal carboxyl group is optionally derivatized as an ester or an amide,
or a salt thereof.

In an aspect of the invention, a compound of formula I has the structure wherein:
(a) X is $X_3$-$X_4$-$X_5$, wherein $X_4$ is serine with a $GlcAc_4$ residue covalently O-linked to said serine through a beta-linkage,
(b) Y is serine, and
(c) Z is Dap(Ac).

In another aspect of the invention, a compound of formula I has the structure wherein:
(a) X is $X_3$-$X_4$-$X_5$, wherein $X_4$ is serine with a Glc residue covalently O-linked to said serine through a beta-linkage,
(b) Y is serine, and
(c) Z is Dap(Ac).

According to some embodiments, $X_4$ and $X_5$ are independently selected from the group consisting of serine, threonine, homoserine, hydroxypiperidine carboxylic acid, a saccharide-modified serine, a saccharide-modified threonine, a saccharide-modified homoserine, and a saccharide-modified hydroxypiperidine carboxylic acid. In an aspect of the invention, $X_4$ is a saccharide-modified serine wherein the saccharide moiety is selected from the group consisting of a monosaccharide, a disaccharide, and a trisaccharide moiety. In an aspect of the invention, a saccharide moiety is selected from the group consisting of β(GlcAc4), α(GlcAc4), Man, Gal, Glc, GalNAc, GlcNAc, and combinations thereof.

According to some embodiments, $X_3$ is selected from the group consisting of diiodotyrosine, bromotyrosine, nitrotyrosine, methyltyrosine, phosphotyrosine, or sulfotyrosine.

According to some embodiments, Y is serine, threonine, homoserine, hydroxypiperidine carboxylic acid, a saccharide-modified serine, a saccharide-modified threonine, a saccharide-modified homoserine, or a saccharide-modified hydroxypiperidine carboxylic acid.

According to some embodiments, Z is selected from the group consisting of Dap(Ac), diaminobutyric acid, norleucine, amino-hexane carboxylic acid and norvaline. According to some embodiments, Z is a natural amino acid which resists carboxypeptidase cleavage. According to some embodiments, $Z_1$ is leucine and $Z_2$ is Dap(Ac). According to some embodiments, the C-terminal carboxyl, group is derivatized to an amide.

In one embodiment of a compound of formula I, X is $X_3$-$X_4$-$X_5$-, wherein $X_3$ is 3,5-diiodotyrosine; $X_4$ is serine with a $GlcAc_4$ residue covalently O-linked to said serine through a beta-linkage, and $X_5$ is threonine;
Y is serine; and
Z is Dap(Ac).

In one embodiment of a compound of formula I:
X is $X_3$-$X_4$-$X_5$, wherein
$X_3$ is 3,5-diiodotyrosine, $X_4$ is serine with a Glc residue covalently O-linked to said serine through a beta-linkage, $X_5$ is threonine;
Y is serine, and
Z is Dap(Ac).

According to another embodiment, the invention is a compound of formula II:

A-X-Glu-Val-Val-Ala-Leu-Y-Arg-Leu-Z    (II)

wherein X-Glu-Val-Val-Ala-Leu-Y-Arg-Leu-Z is SEQ ID NO:46 and
wherein:
(a) X is selected from the group consisting of
(i) zero amino acids,
(ii) a hydroxyamino acid,
(iii) a saccharide-modified hydroxyamino acid,
(iv) $X_1$-$X_2$, wherein $X_1$ is a hydroxyamino acid, a saccharide-modified hydroxyamino acid or Asn, and $X_2$ is a hydroxyamino acid, a saccharide-modified hydroxyamino acid or Asn; and
(v) $X_3$-$X_4$-$X_5$, wherein $X_3$ is a non-natural amino acid or an acetylated amino acid, $X_4$ is a hydroxyamino acid, a saccharide-modified hydroxyamino acid or Asn, and $X_5$ is a hydroxyamino acid, a saccharide-modified hydroxyamino acid or Asn,
(b) Y is a hydroxyamino acid, a saccharide-modified hydroxyamino acid or Asn,
(c) Z is a natural or non-natural amino acid which resists exopeptidase activity in a mammal, and
(d) A is a peptide transduction domain covalently attached to the N-terminal amino acid residue of said compound;
wherein the C-terminal carboxyl group is optionally derivatized as an ester or an amide,
or a salt thereof.

In one embodiment, the peptide transduction domain is polycationic. Other particular embodiments of the invention are those wherein A comprises and optionally consists of an amino acid sequence selected from the group consisting of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

According to another embodiment, the invention is a compound of formula III:

X-Glu-Val-Val-Ala-Leu-Y-Arg-Leu-Z-B    (III)

wherein X-Glu-Val-Val-Ala-Leu-Y-Arg-Leu-Z is SEQ ID NO:47, and
wherein:
(a) X is selected from the group consisting of
(i) zero amino acids,
(ii) a hydroxyamino acid,
(iii) a saccharide-modified hydroxyamino acid,
(iv) $X_1$-$X_2$, wherein $X_1$ is a hydroxyamino acid, a saccharide-modified hydroxyamino acid or Asn and $X_2$ is a hydroxyamino acid, a saccharide-modified hydroxyamino acid or Asn; and
(v) $X_3$-$X_4$-$X_5$, wherein $X_3$ is a non-natural amino acid or an acetylated amino acid, $X_4$ is a hydroxyamino acid, a saccharide-modified hydroxyamino acid or Asn, and $X_5$ is a hydroxyamino acid, a saccharide-modified hydroxyamino acid or Asn,
(b) Y is a hydroxyamino acid, a saccharide-modified hydroxyamino acid or Asn,
(c) Z is a natural or non-natural amino acid which resists exopeptidase activity in a mammal, and
(d) B is a peptide transduction domain covalently attached to Z;
or a salt thereof.

In one embodiment, the peptide transduction domain is polycationic. Other particular embodiments of the invention are those wherein B comprises and optionally consists of an amino acid sequence selected from the group consisting of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, and SEQ ID NO:45.

Also provided are pharmaceutical compositions comprising at least one compound described herein, or a salt thereof, and a pharmaceutically-acceptable carrier.

The invention also includes a method of treating lipodystrophy in a subject in need of such treatment, the method comprising administering to the subject an effective amount of a compound described herein, or a salt thereof.

The invention also includes a method of treating infertility in a subject in need of such treatment, the method comprising administering to the subject an effective amount of a compound described herein, or a salt thereof, and a pharmaceutically-acceptable carrier, wherein the infertility is selected from the group consisting of anorexia-related infertility, lipodystrophy-related infertility, and infertility associated with polycystic ovarian syndrome.

The invention also includes a method of treating obesity in a subject in need of such treatment, the method comprising administering to the subject an effective amount of a compound described herein, or a salt thereof.

The invention also includes a method of treating metabolic syndrome in a subject in need of such treatment, the method comprising administering to the subject an effective amount of a compound described herein, or a salt thereof.

The invention also includes a method of treating hypothalamic amenorrhea in a subject in need of such treatment, the method comprising administering to the subject an effective amount of a compound described herein, or a salt thereof. In an aspect of the invention, a subject having hypothalamic amenorrhea also has osteoporosis.

The invention also includes a method of treating diet induced food craving in a subject in need of such treatment, the method comprising administering to the subject an effective amount of a compound described herein, or a salt thereof.

The invention also includes a method of maintaining weight during dieting in a subject in need of such maintenance, the method comprising administering to the subject an effective amount of a compound described herein, or a salt thereof.

The invention also includes a method of treating insulin resistance in a subject in need of such treatment, the method comprising administering to the subject an effective amount of a compound described herein, or a salt thereof.

The invention also includes a method of improving cognitive functions in a subject in need of such treatment, the method comprising administering to the subject an effective amount of a compound described herein, or a salt thereof.

The invention also includes a method of treating insulin resistance in a subject in need of such treatment, the method comprising administering to the subject an effective amount of a compound described herein, or a salt thereof.

BRIEF DESCRIPTION OF THE DRAWINGS

Embodiments of the present invention will now be described, by way of example only, with reference to the attached Figures.

FIG. 1A illustrates the results of an ELISA-type assay using E1Ac and the negative control antibacterial peptide pyrrhocoricin. The solid bars represent a 20 μg peptide load and the shaded bars represent 10 μg of peptide dried to the assay plate. FIG. 1B illustrates the effects of peptides at concentrations of 100 nM and 1000 nM on MCF-7 cell growth in the presence or absence of 6 nM leptin (L). Bars represent standard error values.

ABBREVIATIONS AND SHORT FORMS

Figure 1A:
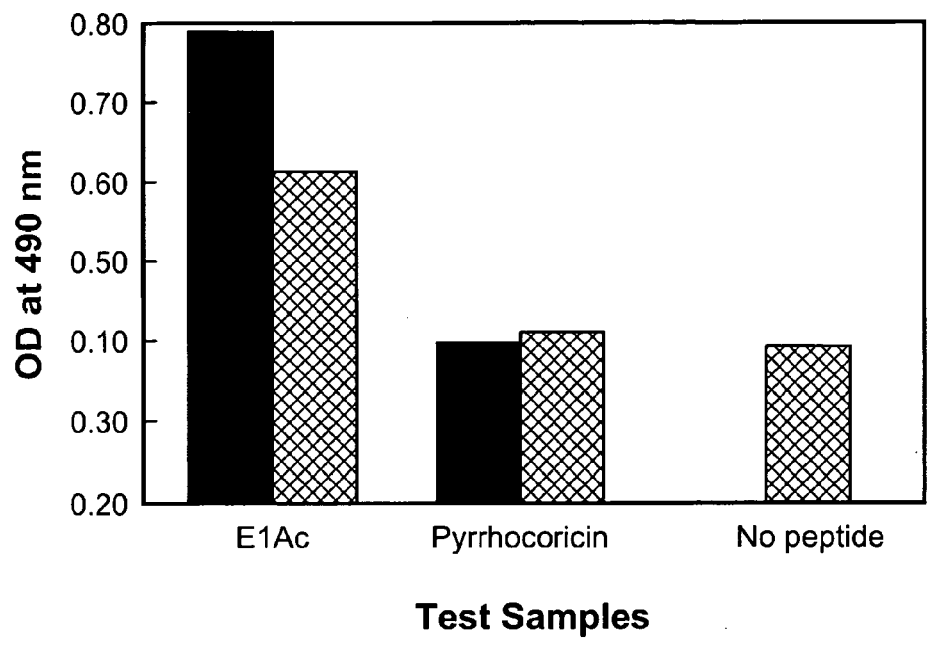
FIGS. 1A and 1B, are a series of images illustrating the interaction of the compound "E1Ac" and "E1Free" glycopeptides with ObR.

The following abbreviations and short forms are used in this specification.

"Dap(Ac)" is N2(3)-acetyl-diaminopropionic acid.
"Glc" is glucose.
"α(GlcAc4)" is 2,3,4,6-O-acetyl-alpha-D-glucose.
"β(GlcAc4)" is 2,3,4,6-O-acetyl-beta-D-glucose.
"Man" is mannose.
"Gal" is galactose.
"GalNAc" is N-acetyl galactosamine.
"GlcNAc" is N-acetyl glucosamine.
"E1Ac" is the peptide of SEQ ID NO: 8
"ObR" is the leptin receptor.
"E1Free" is the peptide SEQ ID NO: 9

DETAILED DESCRIPTION

I. Definitions

As used in the specification and the appended claims, the singular forms "a," "an" and "the" include plural referents unless the context clearly dictates otherwise.

The expressions "treat" and "treatment" mean cause, or the act of causing, a postponement of development of a disorder and/or a reduction in the severity of symptoms that will or are expected to develop. The terms further include ameliorating existing symptoms, preventing additional symptoms, and ameliorating or preventing the underlying metabolic causes of symptoms.

The expression "effective amount", when used to describe therapy to an individual, refers to the amount of a compound that results in a therapeutically useful effect.

As used herein, "individual" (as in the subject of the treatment) means mammals, particularly non-human primates, e.g. apes and monkeys, and most particularly humans.

Peptides are defined herein as organic compounds comprising a chain of two or more amino acids covalently joined by peptide bonds. Peptides may be referred to with respect to the number of constituent amino acids, i.e., a dipeptide contains two amino acid residues, a tripeptide contains three, etc. A "peptide" as used in the presently claimed invention is intended to refer to a moiety with a molecular weight of less than 10,000 Daltons.

The term "amino acid" as used herein means an organic compound containing both a basic amino group and an acidic carboxyl group. Included within this term are natural amino acids (e.g., L-amino acids), modified and unusual amino acids (e.g., D-amino acids), as well as amino acids which are known to occur biologically in free or combined form but usually do not occur in proteins. Included within this term are modified and unusual amino acids, such as those disclosed in, for example, Roberts and Vellaccio (1983) *The Peptides*, 5: 342-429, the teaching of which is hereby incorporated by reference. Natural protein occurring amino acids include, but are not limited to, alanine, arginine, asparagine, aspartic acid, cysteine, glutamic acid, glutamine, glycine, histidine, isoleucine, leucine, lysine, methionine, phenylalanine, serine, threonine, tyrosine, tyrosine, tryptophan, proline, and valine. Natural non-protein amino acids include, but are not limited to arginosuccinic acid, citrulline, cysteine sulfinic acid, 3,4-dihydroxyphenylalanine, homocysteine, homoserine, ornithine, 3-monoiodotyrosine, 3,5-diiodotryosine, 3,5,5'-triiodothyronine, and 3,3',5,5'-tetraiodothyronine. Modified or unusual amino acids which can be used to practice the invention include, but are not limited to, D-amino acids, hydroxylysine, 4-hydroxyproline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexylalanine, N-methyl-norleucine, 3,4-dehydroproline, N,N-dimethylaminoglycine, N-methylaminoglycine, 4-aminopiperidine-4-carboxylic acid, 6-aminocaproic acid, trans-4-(aminomethyl)-cyclohexanecarboxylic acid, 2-, 3-, and 4-(aminomethyl)-benzoic acid, 1-aminocyclopentanecarboxylic acid, 1-aminocyclopropanecarboxylic acid, and 2-benzyl-5-aminopentanoic acid.

The term "peptide bond" means a covalent amide linkage formed by loss of a molecule of water between the carboxyl group of one amino acid and the amino group of a second amino acid.

The term "peptide backbone" means the chain of atoms of a peptide comprising the carboxamide groups that are the peptide bonds together with the atoms of the amino acids that link the carboxyl and amino groups of the amino acid (usually the α-carbon of an α-aminoacid).

The term "side chain" means groups that are attached to the peptide backbone, and typically refers to the group attached to the α-carbon of an α-amino acid. For example, for the side chains of the proteinogenic amino acids include: methyl (alanine), hydroxymethyl (serine), benzyl (phenylalanine), mercaptomethyl (cysteine), and carboxymethyl (aspartic acid).

The term "derivative" as applied to compounds comprising a peptide chain means a compound wherein one or more of the amino, hydroxyl, or carboxyl groups in a side chain of the peptide, or the terminal amino or carboxyl groups, is modified to a derivative functional group. An amino group may be derivatized as an amide (such as an alkyl carboxamide, acetamide), a carbamate (such as an alkyl carbamate, e.g. methyl carbamate or t-butylcarbamate), or a urea. A hydroxyl group may be derivatized as an ester (such as an alkanoate, e.g. acetate, propionate, or an arenecarboxylate, e.g. benzoate), a carbamate (such as an alkyl carbamate, e.g. methyl carbamate), a carbonate (such as an alkyl carbonate, e.g. ethyl carbonate. A carboxyl group may be derivatized as an ester (such as an alkyl ester, e.g. ethyl ester) or an amide (e.g. primary carboxamide, an N-alkyl secondary carboxamide, or an N,N-dialkylcarboxamide). The person skilled in the art will appreciate that derivatives of the peptide will be expected to result in retention of the properties of the parent peptide, either because the incorporation of the derivative group does not change the properties of the peptide, or the derivatizing group is removed in vivo (e.g. via metabolism). Preferred embodiments of the invention are those wherein three or fewer of the amino, carboxyl, and hydroxyl groups, and preferably two or fewer, or one or none, are modified to a derivative functional group. The term "derivative" also includes salts, includes salts of derivatives.

The term "terminal derivative" used in reference to a peptide means a peptide where the C-terminal carboxylate group, or the N-terminal amino group, or both is modified to a derivative functional group. The C-terminal carboxyl group may be derivatized as an ester (such as an alkyl ester, e.g. ethyl ester) or an amide (e.g. primary carboxamide, an N-alkyl secondary carboxamide, or an N,N-dialkylcarboxamide). The N-terminal amino group may be derivatized as an ester (such as an alkyl ester, e.g. ethyl ester) or an amide (e.g. primary carboxamide, an N-alkyl secondary carboxamide, or an N,N-dialkylcarboxamide). The C-terminal carboxyl group and/or the N-terminal amino group may also be in the form of a salt.

In some embodiments of the invention, the compound may be an isolated compound. The term "isolated compound" means a compound substantially free of contaminants or cell components with which the compound naturally occur, or the reagents used in synthesis or the byproducts of synthesis. "Isolated" and "substantially free of contaminants" does not mean that the preparation is technically pure (homogeneous), but it is sufficiently pure to provide the peptide or polypeptide in a form in which it can be used therapeutically.

In some embodiments of the invention, the compound may be an isolated compound. The term "isolated compound" means a compound substantially free of contaminants or cell components with which the compound may naturally occur, or the reagents used in synthesis or the byproducts of synthesis. "Isolated" and "substantially free of contaminants" does not mean that the preparation is technically pure (homogeneous), but it is sufficiently pure to provide the peptide or polypeptide in a form in which it can be used therapeutically.

"Natural amino acid" is used to refer to an amino acid which exists in nature. Examples of natural amino acids include the twenty (20) standard amino acid, norleucine, norvaline, ornithine, and N-acetyl-cysteine.

"Non-natural amino acid" is used to refer to an amino acid which does not exist on its own in nature, but rather, has been synthesized or created by man. Examples of non-natural amino acids include iodinated tyrosine, methylated tyrosine and glycosylated serine, as well as glycosylated threonine.

"Lipodystrophy" refers to a disorder in the way in which a body uses, produces and stores fat.

Weight maintenance during dieting (diet-induced food craving) refers to a condition when patients on low calorie diet suffer from low leptin levels leading to impulse binging.

"Anorexia-related infertility" refers to infertility associated with anorexia nervosa in a female.

The term "obesity" as used herein is defined as excess body mass. The World Health Organization (WHO) classifies body mass (see Kopelman (2000) Nature 404:635643) according body mass index (BMI, weight kg/height $m^2$) as follows: Less than 18.5, underweight; 18.5-24.9, normal; 25.0-25.9, overweight (grade 1); 30-39.9, obese (grade 2); equal to or greater than 40, morbidly obese (grade 3). As used herein, "obesity" refers to both obesity and morbid obesity as defined by the WHO.

Waist circumference can also be used to indicate a risk of metabolic complications where in men a circumference of greater than or equal to 94 cm indicates an increased risk, and greater than or equal to 102 cm indicates a substantially increased risk. Similarly for women, greater than or equal to 88 cm indicates an increased risk, and greater than or equal to 90 cm indicates a substantially increased risk. The waist circumference is measured in cm at midpoint between lower border of ribs and upper border of the pelvis. Other measures of obesity include, but are not limited to, "skinfold thickness," which is a measurement in centimeters of skinfold thickness using calipers, and "bioimpedance," which is based on the principle that lean mass conducts current better than fat mass because it is primarily an electrolyte solution; measurement of resistance to a weak current (impedance) applied across extremities provides an estimate of body fat using an empirically derived equation.

The term "peptide transduction domain" is used to indicate a peptide, or derivative thereof, that is capable of crossing cell membranes and of directing the transport of a peptide, protein, or molecule associated with the protein transduction domain, from the outside of a cell into the cytoplasm of the cell through the cytoplasmic membrane of the cell.

The term "conjugated" referring to the linking of two peptides means that the two peptides are covalently linked to one another. The linking may be accomplished directly, through the formation of an amide bond between the carboxyl group of one peptide and an amino group of the other peptide, or by means of a linking group wherein the linking group has covalent bonds to each of the peptides. For example, the linking group may be a peptide chain, an amino acid, or any group having at least two functional groups and capable of forming covalent bond to each of the two peptide chains.

As used herein, the term "resists exopeptidase activity" refers to the property of a peptide-based compound to resist proteolytic degradation by an exopeptidase. Exopeptidases are proteolytic enzymes which typically remove an N-terminal or a C-terminal amino acid residue from a peptide or protein through hydrolysis. A peptide or protein may be designed, modified, recombinantly prepared, or synthetically prepared to resist degradation by exopeptideases. A peptide is said to "resist exopeptidase activity" according to the invention when a C-terminal or N-terminal amino acid residue is cleaved from such a peptide more slowly than from an otherwise identical peptide which was not modified or designed to resist such exopeptidase activity. A peptide is also said to "resist exopeptidase activity" according to the invention when a C-terminal or N-terminal amino acid residue is not at all cleaved from such a peptide than from an otherwise identical peptide which was not modified or designed to resist such exopeptidase activity.

The term "saccharide" as used herein generally refers to sugars of any identity and any length. The term "saccharide" therefore encompasses a monosaccharide, a disaccharide, and a trisaccharide, as well as oligosaccharides and polysaccharides in general. The term saccharide also refers to glucose, fructose, galactose, N-acetylgalactosamine, and N-acetylglucosamine, among other sugars.

A "saccharide-modified amino acid" as used herein refers to an amino acid which has a saccharide moiety covalently linked thereto. For an amino acid within a peptide, the saccharide is linked to the side chain of the amino acid. A "saccharide-modified hydroxyamino acid" as used herein refers to a hydroxyamino acid which has a saccharide moiety covalently linked thereto.

An "acetylated amino acid" as used herein refers to an amino acid or saccharide-modified amino acid having an acetyl moiety in its side chain.

An amino acid derivative indicated as comprising a linked amino group, such as "Dap(Ac)-NH$_2$", for example, refers to an amino amide derivative wherein the carboxylic acid function of the amino acid is converted to an amide, i.e., NH$_2$—CH(R)—C(O)—NH$_2$ wherein R is the amino acid side chain.

II. Compounds of the Invention

In one aspect of the invention, there is provided a compound of the formula I:

X-Glu-Val-Val-Ala-Leu-Y-Arg-Leu-Z      (SEQ ID NO: 14) (I)

wherein:
(a) X is selected from the group consisting of
(i) zero amino acids,
(ii) a hydroxyamino acid,
(ii) a saccharide-modified hydroxyamino acid,
(iv) $X_1$-$X_2$, wherein $X_1$ is a hydroxyamino acid, a saccharide-modified hydroxyamino acid or Asn, and $X_2$ is a hydroxyamino acid, a saccharide-modified hydroxyamino acid or Asn; and
(v) $X_3$-$X_4$-$X_5$, wherein $X_3$ is a non-natural amino acid or an acetylated amino acid, $X_4$ is a hydroxyamino acid, a saccharide-modified hydroxyamino acid or Asn, and $X_5$ is a hydroxyamino acid, a saccharide-modified hydroxyamino acid or Asn,
(b) Y is a hydroxyamino acid, a saccharide-modified hydroxyamino acid or Asn, and
(c) Z is selected from the group consisting of
(i) a natural or non-natural amino acid which resists exopeptidase activity in a mammal, and
(ii) $Z_1$-$Z_2$, wherein $Z_1$ is a natural or non-natural amino acid and $Z_2$ is a natural or non-natural amino acid which resists exopeptidase activity in a mammal,
wherein the C-terminal carboxyl group is optionally derivatized as an ester or an amide.

An aspect of the invention also includes a salt of a compound of formula I.

In one embodiment of a compound of formula I, X is $X_3$-$X_4$-$X_5$, wherein $X_4$ is serine with a GlcAc$_4$ residue covalently O-linked to said serine through a beta-linkage, Y is serine, and Z is Dap(Ac). In a further aspect of the invention, $X_3$ is 3,5-diiodotyrosine and $X_5$ is threonine. In another aspect of the invention, a compound of formula I is the compound of SEQ ID NO:8, or a salt thereof.

In another embodiment of a compound of formula I, X is $X_3$-$X_4$-$X_5$, wherein $X_4$ is a serine with a Glc residue covalently O-linked to said serine through a beta-linkage, Y is serine, and Z is Dap(Ac). In a further aspect of the invention, $X_3$ is 3,5-diiodotyrosine and $X_5$ is threonine. In another aspect of the invention, a compound of formula I is the compound of SEQ ID NO:9, or a salt thereof.

In another embodiment of a compound of formula I, X is $X_3$-$X_4$-$X_5$, wherein $X_5$ is serine, threonine, homoserine, hydroxypiperidine carboxylic acid, a saccharide-modified serine, a saccharide-modified threonine, a saccharide-modified homoserine, or a saccharide-modified hydroxypiperidine carboxylic acid.

In yet another embodiment of a compound of formula I, X is $X_3$-$X_4$-$X_5$, wherein $X_4$ is serine, threonine, homoserine, hydroxypiperidine carboxylic acid, a saccharide-modified serine, a saccharide-modified threonine, a saccharide-modified homoserine, or a saccharide-modified hydroxypiperidine carboxylic acid. In one embodiment of formula I, X is $X_3$-$X_4$-$X_5$, wherein $X_4$ is serine glycosylated with a saccharide moiety selected from the group consisting of a monosaccharide, a disaccharide, and a trisaccharide. In an aspect of the invention, a saccharide moiety is comprised of one or more of any combination of saccharide moieties selected from the group consisting of β(GlcAc4), α(GlcAc4), Man, Gal, Glc, GalNAc, and GlcNAc.

A saccharide moiety may be attached to an amino acid residue of a peptide of the invention by way of an alpha- or beta-anomeric stereoisomer of the saccharide residue forming the chemical linkage to the amino acid.

Additionally, the saccharide moiety can be linked to an amino acid residue of the peptide by way of a natural glycosidic bond, or by way of a non-natural, alternative glycoamino linkage. In an embodiment of the invention, a saccharide moiety can be linked to the peptide through an amide group on the side chain of an amino acid residue within the peptide. Amino acids useful for this purpose include asparagine, for example.

Therefore, it will be understood that in an aspect of the invention, a residue other than a hydroxyamino acid may be used to link a saccharide to a compound of the invention, provided the side chain of the alternate amino acid can be chemically coupled to a saccharide residue. Methods of coupling a saccharide to an amino acid residue are known in the art, and are described, for example, in U.S. Pat. No. 7,297,511, as well as in greater detail elsewhere herein. The skilled artisan will know, based on the disclosure set forth herein, how to assay the agonist activity of a peptide in which an amino acid residue other than a hydroxyamino acid residue is used to link a saccharide to the peptide according to the invention.

In an embodiment of a compound of formula I, X is $X_3$-$X_4$-$X_5$, and $X_3$ is selected from the group consisting of 3,5-diiodotyrosine, bromotyrosine, nitrotyrosine, methyltyrosine, phosphotyrosine, and sulfotyrosine.

In an embodiment of a compound of formula I, Y is a hydroxyamino acid or a saccharide-modified hydroxyamino acid.

Z is a non-natural amino acid residue that resists exopeptidase activity, and therefore, provides additional stability to a compound of the invention. In an embodiment of the invention, Z is selected from the group consisting of Dap(Ac), diaminobutyric acid, norleucine, amino-hexane carboxylic acid and norvaline. In another embodiment of the invention, Z is a natural amino acid that resists carboxypeptidase activity.

The invention also includes compounds of formulae II and III, which are conjugates of formula I. In an aspect of the invention, a compound of the invention comprises a conjugate comprising peptide transduction domain attached to the N-terminus of the peptide of formula II or to the C-terminus of the peptide of formula III. In one embodiment, a conjugate comprises a compound of the formula II, or a salt thereof:

A-X-Glu-Val-Val-Ala-Leu-Y-Arg-Leu-Z (II)

wherein X-Glu-Val-Val-Ala-Leu-Y-Arg-Leu-Z is SEQ ID NO:46 and
wherein:
(a) X is selected from the group consisting of
(i) zero amino acids,
(ii) a hydroxyamino acid,
(iii) a saccharide-modified hydroxyamino acid,
(iv) $X_1$-$X_2$, wherein $X_1$ is a hydroxyamino acid, a saccharide-modified hydroxyamino acid or Asn, and $X_2$ is a hydroxyamino acid, a saccharide-modified hydroxyamino acid or Asn; and
(v) $X_3$-$X_4$-$X_5$, wherein $X_3$ is a non-natural amino acid or an acetylated amino acid, $X_4$ is a hydroxyamino acid, a saccharide-modified hydroxyamino acid or Asn, and $X_5$ is a hydroxyamino acid, a saccharide-modified hydroxyamino acid or Asn, (b) Y is a hydroxyamino acid, a saccharide-modified hydroxyamino acid or Asn,
(c) Z is a natural or a non-natural amino acid which resists exopeptidase activity in a mammal,
wherein the C-terminal carboxyl group is optionally derivatized as an ester or an amide, and
(d) A is a peptide transduction domain covalently attached to the N-terminal residue of the compound of formula II.

In another embodiment, a conjugate comprises a compound of the formula III, or a salt thereof:

X-Glu-Val-Val-Ala-Leu-Y-Arg-Leu-Z-B (III)

wherein X-Glu-Val-Val-Ala-Leu-Y-Arg-Leu-Z is SEQ ID NO:47, and
wherein:
(a) X is selected from the group consisting of
(i) a hydroxyamino acid,
(ii) a saccharide-modified hydroxyamino acid,
(iii) $X_1$-$X_2$, wherein $X_1$ is a hydroxyamino acid, a saccharide-modified hydroxyamino acid or Asn, and $X_2$ is a hydroxyamino acid, a saccharide-modified hydroxyamino acid or Asn; and
(iv) $X_3$-$X_4$-$X_5$, wherein $X_3$ is a non-natural amino acid or an acetylated amino acid, $X_4$ is a hydroxyamino acid, a saccharide-modified hydroxyamino acid or Asn, and $X_5$ is a hydroxyamino acid, a saccharide-modified hydroxyamino acid or Asn,
(b) Y is a hydroxyamino acid, a saccharide-modified hydroxyamino acid or Asn,
(c) Z is a natural or a non-natural amino acid which resists exopeptidase activity in a mammal, and
(d) B is a peptide transduction domain covalently attached to Z.

A peptide transduction domain is a peptide that is capable of directing the transport of a peptide, protein, or other molecule associated with the peptide transduction domain, across a cell membrane, from the outside of a cell into the cytoplasm of a cell. The property of promoting facile cellular entry is retained even when the peptide sequence is conjugated to another molecule. As a result, conjugation to such sequences can be used to facilitate delivery into cells of other peptides, such as those of formula II or III of the present invention. See, for example, *Handbook of Cell-Penetrating Peptides*, by Ulo Langel (Editor) (CRC Press, 2nd Edition, 2006). *Cell-Penetrating Peptides: Process and Applications*, by Ulo Langel (Editor) (CRC Press, 1st Edition, 2002); and E. L. Snyder, et al., "Cell-penetrating Peptides in Drug Delivery", *Pharm. Res.*, 2004, 21(3), 389-93.

Peptide transduction domains useful in the invention include, but are not limited to, a Tat peptide from HIV glycoprotein 120, a transportan, polyarginine, polylysine, and proline-arginine rich antibacterial peptides such as pyrrhocoricin, as set forth in U.S. Pat. No. 7,015,309, incorporated herein by reference in its entirety. In one aspect of the invention, a peptide transduction domain is polycationic.

a. Preparation of Compounds of the Invention

The compounds of the invention may be prepared by methods known to the person skilled in the art of peptide and organic synthesis.

Peptides of the present invention may be natural peptides, recombinant peptides or synthetic peptides. They may also be chemically synthesized, using, for example, solid phase synthesis methods. Preferred methods of synthesis of compounds of formulae I-III are set forth in Experimental Example 1 herein. Additionally, peptide transduction domains appended to peptides of the invention may be natural or synthetic peptides, and may be either prepared by isolation from natural sources or may be synthesized.

The peptides of the present invention may be synthesized de novo using peptide synthesis methods. In such methods, the peptide chain is prepared by a series of coupling reactions in which the constituent amino acids are added to the growing peptide chain in the desired sequence. The use of various N-protecting groups, e.g., the carbobenzyloxy group or the t-butyloxycarbonyl group; various coupling reagents e.g., dicyclohexylcarbodiimide or carbonyldiimidazole; various active esters, e.g., esters of N-hydroxyphthalimide or N-hydroxy-succinimide; and the various cleavage reagents, e.g., trifluoroacetic acid (TFA), HCl in dioxane, boron tris-(trifluoroacetate) and cyanogen bromide; and reaction in solution with isolation and purification of intermediates are methods well-known to those of ordinary skill in the art. The reaction may be carried out with the peptide either in solution or attached to a solid phase support. In the solid phase method, the peptide is released from the solid phase support following completion of the synthesis.

In an embodiment, peptide synthesis method may follow Merrifield solid-phase procedures. See Merrifield, *J. Am. Chem. Soc.,* 1963, 85, 2149-54 and *Science,* 1965, 50, 178-85. Additional information about the-solid phase synthetic procedure can be obtained from the treatises *Solid Phase Peptide Synthesis: A Practical Approach* by E. Atherton and R. C. Sheppard (Oxford University Press, 1989, *Solid phase peptide synthesis,* by J. M. Stewart and J. D. Young, (2nd edition, Pierce Chemical Company, Rockford, 1984), and the review chapters by R. Merrifield in *Advances in Enzymology* 32:221-296, edited by F. F. Nold (Interscience Publishers, New York, 1969) and by B. W. Erickson and R. Merrifield in *The Proteins* Vol. 2, pp. 255 et seq., edited by Neurath and Hill, (Academic Press, New York, 1976). Peptide synthesis may follow synthetic techniques such as those set forth in Fields et al., *Introduction to Peptide Synthesis,* in *Current Protocols in Molecular Biology* (Chapter 11, Unit 11.15; John Wiley and Sons, 2008) and Amblard et al. (2006, Molecular Biotechnology, 33:239-254).

The synthesis of peptides by solution methods is described in The Proteins, Vol. 11, edited by Neurath et al. ($3^{rd}$ Edition, Academic Press 1976). Other general references to the synthesis of peptides include: *Peptide Synthesis Protocols*, edited by M. W. Pennington and Ben M. Dunn (Humana Press 1994), *Principles of Peptide Synthesis*, by Miklos Bodanszky ($2^{nd}$ edition, Springer-Verlag, 1993), and *Chemical Approaches to the Synthesis of Peptides and Proteins* by Paul Lloyd-Williams, F. Albericio, E. Giralt (CRC Press 1997), and *Synthetic Peptides: A User's Guide*, edited by G. Grant (Oxford University Press, 2002).

For compounds of formula II or III comprising a protein transduction domain, the link between the N-terminal or C-terminal amino acid of the peptide and the peptide transduction domain is formed via a single bond or an optional linking group. The purpose of the linking group is merely to covalently join the peptide transduction domain to an N- or C-terminal amino acid of the peptide of formula II or III, respectively, and therefore, one of ordinary skill in the art will be aware of a multitude of ways in which to achieve such linkage.

The linking group for coupling a peptide transduction domain to a compound of formula I may be any moiety that is at least bifunctional, provided that the resulting link between the protein transduction domain and the N-terminal or C-terminal amino acid is stable. Suitable linking moieties include bi- and multi-functional alkyl, aryl, aralkyl or peptidic moieties, alkyl, aryl or aralkyl aldehydes acids esters and anhydrides, sulfhydryl or carboxyl groups, such as maleimido benzoic acid derivatives, maleimido propionic acid derivatives and succinimido derivatives or may be derived from cyanuric bromide or chloride, carbonyldiimidazole, succinimidyl esters or sulphonic halides and the like (Fischer et al., U.S. Pat. No. 6,472,507, the entire disclosure of which is incorporated herein by reference). The functional groups on the linker moiety may include amino, hydrazino, hydroxyl, thiol, maleimido, carbonyl, and carboxyl groups.

Optionally the linker group is selected so as to be sufficiently labile (e.g., to enzymatic cleavage by an enzyme present in the targeted tissue) so that it is cleaved following transport of a peptide of the invention, thereby releasing the peptide. Exemplary labile linkages are described in Low et al., U.S. Pat. No. 5,108,921, the entire disclosure of which is incorporated herein by reference. The peptide-active agent delivery system may also dissociate by way of chemical cleavage between the active agent and peptide of the invention. Within the embodiments wherein the linker moiety includes amino acid residues, such cleavage may occur within the linker moiety itself.

The use of the term "linking" is not intended to imply any limitation as to the process by which the compound of formula II or III is synthesized. Thus it is not necessary that the peptide transduction domain and a peptide of formula II or III be separately synthesized and then linked together. Rather, the term merely describes the structural connection between of the peptide transduction domain, the peptide of formula II or III, and the linking group used to conjugate a peptide transduction domain to the peptide of formula II or III.

Alternatively, peptides may be prepared utilizing recombinant DNA technology, which comprises combining a nucleic acid encoding peptides of formulae I-III in a suitable vector, inserting the resulting vector into a suitable host cell, recovering the peptide subsequently produced by the host cell, and purifying the polypeptide recovered. The required techniques of recombinant DNA and protein technology are known to the ordinary skilled artisan. General methods for the cloning and expression of recombinant molecules are described in *Molecular Cloning* by Sambrook et al. (Cold Spring Harbor Laboratories, Second Ed., 1989) and in *Current Protocols in Molecular Biology* by Ausubel (Wiley and Sons, 1987).

The nucleic acid encoding a desired peptide may be operatively linked to one or more regulatory regions. Regulatory regions include promoters, polyadenylation signals, translation initiation signals (Kozak regions), termination codons, peptide cleavage sites, and enhancers. The regulatory sequences used must be functional within the cells of the vertebrate in which they are administered. Selection of the appropriate regulatory region or regions is a routine matter, within the level of ordinary skill in the art.

Promoters that may be used in the synthesis of compounds of the present invention include both constitutive promoters and inducible promoters. The promoters may be prokaryotic or eukaryotic, depending on the host.

The compounds of the invention, whether prepared by chemical synthesis or recombinant DNA technology, may be purified using known techniques, for example preparative HPLC, FPLC, affinity chromatography, as well as other chromatographic methods. Isolated compounds may then be assessed for biological activity according to the methods described herein, as well as by any methods known to the skilled artisan.

Peptides of the invention may be modified by addition of O-linked saccharides. O-linked saccharides are linked primarily to hydroxyamino acid side chains, such as those found in serine and threonine. For a review of O-linked saccharides, see Schachter and Brockhausen, *The Biosynthesis of Branched O-Linked Glycans*, 1989, Society for Experimental Biology, pp. 1-26 (Great Britain); Takeda et al., Trends Biochem. Sci. 20:367-371 (1995); and Udenfriend et al., Ann. Rev. Biochem. 64:593-591 (1995).

In one aspect, peptides having O-linked saccharides can be prepared using in vitro or in vivo enzymatic techniques. For example, peptides having O-linked saccharides can be formed by the stepwise addition of sugars from nucleotide sugars (Tanner et al., *Biochim. Biophys. Acta.* 906:81-91 (1987); and Hounsell et al., *Glycoconj.* J. 13:19-26 (1996)). In another aspect, peptides having O-linked saccharides can be prepared using chemical synthetic methods, such as solid-phase synthesis or liquid-phase synthesis.

Peptides of the invention may be modified by addition of N-linked saccharides. Peptides having N-linked saccharides are modified with saccharide residues linked to the side chain of asparagine residues. As for O-linked saccharides, peptides having N-linked saccharides can be prepared in vitro or in vivo using enzymatic techniques. Similarly, peptides having N-linked saccharides can be prepared using chemical synthetic methods, such as solid-phase synthesis or liquid-phase synthesis.

A variety of methods are known in the art to customize the glycosylation pattern of a peptide, including those described in Urge, L., et al. (*Tetrahedron Lett.,* 1991, 32:3445-3448), Cudic, M., et al. (*Bioorg. Med. Chem.,* 2002, 10:3859-3870), WO 99/22764, WO 98/58964, WO 99/54342 and U.S. Pat. Nos. 5,047,335 and 7,276,475, among others. For enzymatic techniques, many of the enzymes required for the in vitro addition of saccharide moieties to peptides have been cloned and sequenced. In some instances, these enzymes have been used in vitro to add specific saccharides to the side chain of an amino acid within a peptide. In other instances, cells have been genetically engineered to express a combination of enzymes and desired peptides such that addition of a desired saccharide moiety to an expressed peptide occurs within the cell.

For synthetic techniques, peptides can be produced by the established procedure of solid phase peptide synthesis. Briefly, this procedure entails the sequential assembly of the appropriate amino acids into a peptide of a desired sequence while the end of the growing peptide is linked to an insoluble support. Usually, the carboxyl terminus of the peptide is linked to a polymer from which it can be liberated upon treatment with a cleavage reagent.

b. Protein Transduction Domains

A protein transduction domain is a peptide that is capable of crossing cell membranes and of directing the transport of a peptide, protein, or molecule associated with the protein transduction domain; from the outside of a cell into the cytoplasm of the cell through the cytoplasmic membrane of the cell.

Several naturally occurring proteins have been able to enter cells easily, including the TAT protein of HIV, the antennapedia protein from Drosophila, and the VP22 protein from the herpes simplex virus. Although the mechanism of cellular entry for such proteins is not fully understood, it has been found that relatively short sequences (a protein transduction sequence or a membrane fusion sequence) in such proteins accounts for the facile cellular entry. The property of promoting facile cellular entry is retained even when the peptide sequence is conjugated to another molecule. As a result, conjugation to such sequences can be used to facilitate delivery into cells of other molecules.

Protein transduction domains have been the subject of considerable interest and investigation because of their ability, through conjugation to other compounds, to facilitate transport of the conjugated compound into the cell, and as a result a substantial body of literature has been published. See, for example, *Handbook of Cell-Penetrating Peptides*, by Ulo Langel (Editor) (CRC Press, 2$^{nd}$ Edition, 2006). *Cell-Penetrating Peptides: Process and Applications*, by Ulo Langel (Editor) (CRC Press, 1$^{st}$ Edition, 2002); E. L. Snyder, et al., "Cell-penetrating Peptides in Drug Delivery", *Pharm. Res.,* 2004, 21(3), 389-93. A. J. M. Beerens, et al., "Protein Transduction Domains and their utility in Gene Therapy", *Current Gene Therapy,* 2003, 3(5), 486-94; F. Hudecz, et al., "Medium-sized peptides as built in carriers for biologically active compounds", *Med. Res. Rev.,* 2005, 25(6), 679-736.

Examples of amino acid sequences that may be incorporated in, or used as, protein transduction domains are those shown in Table 1.

TABLE 1

Examples of Protein transduction domains

| Sequence | Name and/or Source |
|---|---|
| Tyr Gly Arg Lys Lys Arg Arg Gln Arg Arg Arg Gly (SEQ ID NO: 15) | HIV TAT |
| Gly Arg Lys Lys Arg Arg Gln Arg Arg Arg Pro Pro Gln Cys (SEQ ID NO: 16) | HIV TAT |
| Gly Arg Lys Lys Arg Arg Gln Arg Arg Arg Pro Pro Gln (SEQ ID NO: 17) | HIV TAT |
| Tyr Gly Arg Lys Lys Arg Arg Gln Arg Arg Arg (SEQ ID NO: 18) | HIV TAT |
| Tyr Ala Arg Lys Ala Arg Arg Gln Ala Arg Arg (SEQ ID NO: 19) | Synthetic sequence (based on HIV TAT) |
| Tyr Ala Arg Ala Ala Ala Arg Gln Ala Arg Ala (SEQ ID NO: 20) | Synthetic sequence (based on HIV TAT) |
| Tyr Ala Arg Ala Ala Arg Arg Ala Ala Arg Arg (SEQ ID NO: 21) | Synthetic sequence (based on HIV TAT) |

TABLE 1-continued

Examples of Protein transduction domains

| Sequence | Name and/or Source |
|---|---|
| Tyr Ala Arg Ala Ala Arg Arg Ala Ala Arg Ala (SEQ ID NO: 22) | Synthetic sequence (based on HIV TAT) |
| Arg Gln Ile Lys Ile Trp Phe Gln Asn Arg Arg Met Lys Trp Lys Lys (SEQ ID NO: 23) | Pantp (43-88) ("Penetratin") |
| Lys Lys Trp Lys Met Arg Arg Asn Gln Phe Trp Val Lys Val Gln Arg (SEQ ID NO: 24) | Retro-inverso pAntp (43-48) |
| Arg Arg Trp Arg Arg Trp Trp Arg Arg Trp Trp Arg Arg Trp Arg Arg (SEQ ID NO: 25) | W/R Penetratin |
| Arg Arg Met Lys Trp Lys Lys (SEQ ID NO: 26) | Pantp (52-58) |
| Arg Arg Arg Arg Arg Arg Arg (SEQ ID NO: 27) | Arginine 7-mer |
| Arg Arg Arg Arg Arg Arg Arg Arg Arg (SEQ ID NO: 28) | Arginine 9-mer |
| Asp Ala Ala Thr Arg Ser Ala Ala Ser Arg Pro Thr Glu Arg Pro Arg Ala Pro Ala Arg Ser Ala Ser Arg Pro Arg Arg Pro Val Glu (SEQ ID NO: 29) | VP22 transduction domain (Herpes Simplex Virus 1) |
| Gly Ala Leu Phe Leu Gly Trp Leu Gly Ala Ala Gly Ser Thr Met Gly (SEQ ID NO: 30) | GP41 fusion sequence |
| Gly Ala Leu Phe Leu Gly Phe Leu Gly Ala Ala Gly Ser Thr Met Gly Ala Trp Ser Gln Pro Lys Ser Lys Arg Lys Val (SEQ ID NO: 31) | GP41 fusion sequence. |
| Met Gly Leu Gly Leu His Leu Leu Val Leu Ala Ala Ala Leu Gln Gly Ala Trp Ser Gln Pro Lys Lys Lys Arg Lys Val (SEQ ID NO: 32) | Caiman crocodylus Ig(v) light chain- SN40NLS |
| Pro Leu Ser Ser Ile Phe Ser Arg Ile Gly Asp Pro (SEQ ID NO: 33) | Hepatitis B virus PreS2 antigen consisting of the translocation motif from residues 41-52. |
| Phe Trp Arg Gly Asp Leu Val Phe Asp Phe Gln Val (SEQ ID NO: 34) | Hepatitis A virus VP3 core protein. |
| Lys Phe Thr Ile Val Phe Pro His Asn Gln Lys Gly Asn Trp Lys Asn Val Pro Ser Asn Tyr His Tyr Cys Pro (SEQ ID NO: 35) | Vesicular stomatitis virus VSV-G peptide. |
| Ala Lys Arg Ala Arg Leu Ser Thr Ser Phe Asn Pro Val Tyr Pro Tyr Glu Asp Glu Ser (SEQ ID NO: 36) | Adenovirus fiber |
| Gly Trp Thr Leu Asn Ser Ala Gly Tyr Leu Leu Gly Lys Ile Asn Leu Lys Ala Leu Ala Ala Leu Ala Lys Lys Ile Leu (SEQ ID NO: 37) | Transportan |
| Arg Gly Gly Arg Leu Ser Tyr Ser Arg Arg Arg Phe Ser Thr Ser Thr Gly Arg (SEQ ID NO: 38) | SynB1 |
| Ala Ala Val Ala Leu Leu Pro Ala Val Leu Leu Ala Leu Leu Ala Pro (SEQ ID NO:39) | Kaposi's sarcoma-associated herpesvirus Kaposi FGF signal sequence |
| Ala Ala Val Leu Leu Pro Val Leu Leu Ala Ala Pro (SEQ ID NO: 40) | Kaposi's sarcoma-associated herpesvirus Kaposi FGF signal sequence |

TABLE 1-continued

Examples of Protein transduction domains

| Sequence | Name and/or Source |
|---|---|
| Val Thr Val Leu Ala Leu Gly Ala Leu Ala Gly Val Gly Val Gly (SEQ ID NO: 41) | Human integrin beta3 signal sequence |
| Val Ala Tyr Ile Ser Arg Gly Gly Val Ser Thr Tyr Tyr Ser Asp Thr Val Lys Gly Arg Phe Thr Arg Gln Lys Tyr Asn Lys Arg Ala (SEQ ID NO: 42) | P3 Membrane Fusion Sequence |
| Lys Leu Ala Leu Lys Leu Ala Leu Lys Ala Leu Lys Ala Ala Leu Lys Leu Ala (SEQ ID NO: 43) | Model ambiphilic peptide |
| Trp Glu Ala Lys Leu Ala Lys Ala Leu Ala Lys Ala Leu Ala Lys His Leu Ala Lys Ala Leu Ala Lys Ala Leu Lys Ala Cys Glu Ala (SEQ ID NO: 44) | KALA |
| Arg Arg Gln Arg Arg Thr Ser Lys Leu Met Lys Arg (SEQ ID NO: 45) | Synthetic (U.S. Pat. No. 6,881,825) | c. Salts of Compounds of the Invention

Peptide chains typically contain acidic or basic groups (such as amine or carboxyl groups) such groups will not necessarily be in the free base form. When referring to compounds that are peptides or compounds that contain peptide chains, the reference is intended to include salt forms of the peptide. Within the scope of the invention, therefore, are salts of compounds of formulae I-III and the derivatives thereof. The preferred salts are pharmaceutically-acceptable salts.

The term "salts" embraces addition salts of free acids or free bases which are compounds of the invention. The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding compound according to formulae I-III by reacting, for example, the appropriate acid or base with the compound according to formulae I-III.

d. Pharmaceutical Compositions

The compounds of the invention may be administered in the form of a pharmaceutical composition, in combination with a pharmaceutically acceptable carrier. The active ingredient in such formulations may comprise from 0.1 to 99.99 weight percent. "Pharmaceutically acceptable carrier" means any carrier, diluent or excipient which is compatible with the other ingredients of the formulation and not deleterious to the recipient.

The active agent is preferably administered with a pharmaceutically acceptable carrier selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences*, 18th Edition (1990), Mack Publishing Co., Easton, Pa. Suitable dosage forms may comprise, for example, tablets, capsules, solutions, parenteral solutions, troches, suppositories, or suspensions.

For parenteral administration, the active agent may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of the active agent. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, the active agent may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents. According to one tablet embodiment, the active agent may be combined with carboxymethylcellulose calcium, magnesium stearate, mannitol and starch, and then formed into tablets by conventional tableting methods.

The compositions are preferably formulated in a unit dosage form, each dosage containing from about 1 to about 500 mg. The term "unit dosage form" refers to physically discrete units suitable as a unitary dosage for human subjects and other mammals, each unit containing a predetermined quantity of active material calculated to produce the desired therapeutic effect, in association with a suitable pharmaceutical excipient.

The pharmaceutical compositions of the present invention may also be formulated so as to provide slow or controlled release of the active ingredient therein using, for example, hydropropylmethyl cellulose in varying proportions to provide the desired release profile, other polymer matrices, gels, permeable membranes, osmotic systems, multilayer coatings, microparticles, liposomes and/or microspheres.

In general, a controlled-release preparation is a pharmaceutical composition capable of releasing the active ingredient at the required rate to maintain constant pharmacological activity for a desirable period of time. Such dosage forms provide a supply of a drug to the body during a predetermined period of time and thus maintain drug levels in the therapeutic range for longer periods of time than conventional non-controlled formulations. In an embodiment of the invention, a controlled release composition of the invention provides continuous release of an active agent over a fourteen day period of time.

U.S. Pat. No. 5,674,533 discloses controlled-release pharmaceutical compositions in liquid dosage forms for the administration of moguisteine, a potent peripheral antitussive. U.S. Pat. No. 5,059,595 describes the controlled-release of active agents by the use of a gastro-resistant tablet for the therapy of organic mental disturbances. U.S. Pat. No. 5,591,767 describes a liquid reservoir transdermal patch for the controlled administration of ketorolac, a non-steroidal anti-inflammatory agent with potent analgesic properties. U.S. Pat. No. 5,120,548 discloses a controlled-release drug delivery device comprised of swellable polymers. U.S. Pat. No. 5,073,543 describes controlled-release formulations containing a trophic factor entrapped by a ganglioside-liposome vehicle. U.S. Pat. No. 5,639,476 discloses a stable solid controlled-release formulation having a coating derived from an aqueous dispersion of a hydrophobic acrylic polymer. Biodegradable microparticles are known for use in controlled-release formulations. U.S. Pat. No. 5,354,566 discloses a controlled-release powder that contains the active ingredient. U.S. Pat. No. 5,733,566, describes the use of polymeric microparticles that release antiparasitic compositions.

The controlled-release of the active ingredient may be stimulated by various inducers, for example pH, temperature, enzymes, water, or other physiological conditions or compounds. Various mechanisms of drug release exist. For example, in one embodiment, the controlled-release component may swell and form porous openings large enough to release the active ingredient after administration to a patient. The term "controlled-release component" in the context of the present invention is defined herein as a compound or compounds, such as polymers, polymer matrices, gels, permeable membranes, liposomes and/or microspheres, that facilitate the controlled-release of the active ingredient in the pharmaceutical composition. In another embodiment, the controlled-release component is biodegradable, induced by exposure to the aqueous environment, pH, temperature, or enzymes in the body. In another embodiment, sol-gels may be used, wherein the active ingredient is incorporated into a sol-gel matrix that is a solid at room temperature. This matrix is implanted into a patient, preferably a mammal, having a body temperature high enough to induce gel formation of the sol-gel matrix, thereby releasing the active ingredient into the patient.

Compositions of the compounds of the invention that are suitable for administration intranasally or by inhalation are of particular interest.

The compounds of the invention can be administered intranasally or by inhalation, typically in the form of a dry powder (either alone, as a mixture, for example, in a dry blend with lactose in anhydrous or monohydrate form, preferably monohydrate, mannitol, dextran, glucose, maltose, sorbitol, xylitol, fructose, sucrose or trehalose, or as a mixed component particle, for example, mixed with phospholipids) from a dry powder inhaler or as an aerosol spray from a pressurized container, pump, spray, atomizer (preferably an atomizer using electrohydrodynamics to produce a fine mist), or nebulae, with or without the use of a suitable propellant, such as dichlorofluoromethane.

The pressurized container, pump, spray, atomizer, or nebulae contains a solution or suspension of the active compound comprising, for example, ethanol (optionally, aqueous ethanol) or a suitable alternative agent for dispersing, solubilizing, or extending release of the active, the propellant(s) as solvent and an optional surfactant, such as sorbitan trioleate or an oligolactic acid.

Prior to use in a dry powder or suspension formulation, the drug product is micronized to a size suitable for delivery by inhalation (typically less than 5 microns). This may be achieved by any appropriate comminuting method, such as spiral jet milling, fluid bed jet milling, supercritical fluid processing to form nanoparticles, high pressure homogenization, or spray drying.

A suitable solution formulation for use in an atomizer using electrohydrodynamics to produce a fine mist may contain from 1 µg to 20 mg of the compound of the invention per actuation and the actuation volume may vary from 1 µL to 100 µL. A typical formulation may comprise the compound of the invention, propylene glycol, sterile water, ethanol and sodium chloride. Alternative solvents which may be used instead of propylene glycol include glycerol and polyethylene glycol.

Capsules, blisters and cartridges (made, for example, from gelatin or HPMC) for use in an inhaler or insufflator may be formulated to contain a powder mix of the nicotinamide derivative of formula (I), a suitable powder base such as lactose or starch and a performance modifier such as L-leucine, mannitol, or magnesium stearate.

Formulations for inhaled/intranasal administration may be formulated to be immediate and/or modified release. Modified release formulations include delayed-, sustained-, pulsed-, controlled dual-, targeted and programmed release. Sustained or controlled release can be obtained by using for example poly(D,L-lactic-co-glycolic acid).

III. Activity of the Compounds of the Invention

In an aspect, a compound of the invention has "full agonist activity" of the leptin receptor ("ObR"). As used herein, "full agonist activity" means that a compound of invention demonstrates agonistic activity, but does not demonstrate antagonistic activity, with respect to ObR both in the presence and absence of exogenous native leptin or other ObR-stimulating agents.

Compounds of the invention that bind to ObR or that bind to and stimulate some or all of the function of ObR (ObR agonistic activity) may be assayed using a cellular assay as set forth in detail in Experimental Example 2 herein. In an embodiment of the invention, an ObR binding and/or agonist assay is conducted using a cell line expressing ObR, wherein such cells are stimulated to grow as a result of treatment with leptin or leptin analogs. The skilled artisan will be aware of methods of detecting peptide-receptor binding. Western blotting and dot-blotting techniques, among others, are useful for determining the binding of a compound of the invention to ObR. The skilled artisan will also be aware of methods of detecting and measuring cell growth. Cell counting, among other techniques, can be used to determine cell growth as a result of agonist activity of a compound of the present invention.

Other methods of measuring efficacy of compounds of the invention include, but are not limited to, receptor-binding assays, monitoring changes in downstream signaling of intracellular signaling pathways, induction of DNA and/or protein synthesis, or monitoring metabolic status of cells. Additionally, the efficacy of compounds of the invention can also be assayed in animal models, i.e., by monitoring the ability of the compounds to substitute for leptin in leptin-deficient animals, or by monitoring food intake, appetite, metabolic rates, and glucose/lipid levels in animals with obesity and insulin resistance.

IV. Methods of Treatment Using Compounds of the Invention

The compounds of the invention are useful as ObR agonists. They bind to ObR and agonize ObR-mediated activity, and thus, can be used for the treatment of diseases and conditions which can benefit from an ObR-mediated upregulation in cell signaling and growth, including conditions that are related to leptin deficiency or leptin resistance. Accordingly, compounds of the invention may be used to treat conditions including, but not limited to, obesity, including appetite control in obesity; lipodystrophy; metabolic syndrome; hypothalamic amenorrhea; lipodystrophy; infertility associated with polycystic ovarian syndrome; weight control during dieting, including diet-induced food craving, osteoporosis as a complication of hypothalamic amenorrhea, and impaired cognitive functions. The aforementioned conditions are related to, at least in part, to leptin deficiency and/or leptin resistance.

Therefore, an individual who is in need of treatment with a compound according to the invention can be an individual who is suffering from one or more symptoms of obesity, lipodystrophy, metabolic syndrome, diet-induced food craving, infertility, including anorexia-related infertility and lipodystrophy-related infertility, or osteoporosis as a complication of hypothalamic amenorrhea, impaired cognitive functions, among other disorders.

For example, lipoatrophic diabetes is a syndrome characterized by insulin resistance in association with a paucity of adipose tissue. Patients with severe lipoatrophy die prematurely, typically from the complications of diabetes or liver disease. Experimental evidence suggests that the insulin resistance in these patients is caused by the lack of adipose tissue. Because adipose tissue normally produces leptin, the leptin deficiency in this syndrome can cause high blood lipid levels and insulin resistance that can lead to diabetes. Administration of ObR agonists according to the present invention can treat this diabetic condition, as well as other conditions which are related to a deficit of leptin or leptin activity.

Similarly, in individuals having metabolic changes that decrease the level of leptin in the body, i.e., individuals who are dieting, women with hypothalamic ammenorrhea, and individuals having osteopenia or osteoporosis, administration of ObR agonists according to the present invention can treat the adverse conditions by stimulating (i.e., "agonizing") ObR.

In obese individuals, leptin is produced by fat tissue, but fails to activate ObR in the hypothalamus, resulting in increased appetite and weight gain. This leptin resistance can be overcome by the administration of ObR-specific agonists, such as the compounds of the present invention. Weight-reduced individuals are in a state of relative leptin deficiency due to loss of body fat. Energy and neuroendocrine homeostatic systems are altered during the maintenance of a reduced body weight in a manner that favors weight regain. These metabolic changes accompanying maintenance of reduced body weight, can be reversed by administration of an ObR agonist to the individual.

In an embodiment, the invention includes a method of treating obesity in a patient in need thereof. The method comprises administering an effective amount of the compound, or a pharmaceutical composition comprising the compound, as described herein, to an individual in need to such treatment or prophylaxis. An obese individual can benefit from treatment with a compound, as described herein, because the compound can agonize the activity of ObR. As set forth in detail elsewhere herein, an effective amount of a compound of the invention can be administered to an individual for the purpose of reducing voluntary food intake by the individual, which can aid weight and/or fat loss in the individual.

In an embodiment, the invention includes a method of treating an overweight condition in an individual in need thereof. The method comprises administering an effective amount of the compound, or a pharmaceutical composition comprising the compound, as described herein, to an individual in need to such treatment or prophylaxis. An overweight patient can benefit from this treatment much the same as an obese individual, as described above.

In an embodiment, the invention includes a method of treating lipodystrophy in a patient in need thereof. The method comprises administering an effective amount of the compound, or a pharmaceutical composition comprising the compound, as described herein, to an individual in need of such treatment or prophylaxis.

Lipodystrophy is a condition in which an individual experiences a loss in subcutaneous fat tissue. Lipodystrophy may be congenital or acquired (e.g., fat loss at a site of repeated insulin injections in diabetics), and presents as changes in the appearance of the skin at a site of the condition. Depressions in the skin, sagging of the skin, and pronounced appearance of the underlying structures are all physical manifestations of lipodystrophy. Metabolic disorders and resistance to insulin are also possible outcomes of lipodystrophy in a patient. Treatment of a lipodystrophy patient according to the invention can reverse or otherwise treat one or more of the lipodystrophy-associated conditions described herein by agonizing the activity of ObR, and by overcoming leptin resistance in resistant individuals.

In another embodiment, the invention includes a method of treating anorexia-mediated infertility in a patient in need thereof. The method comprises administering an effective amount of the compound, or a pharmaceutical composition comprising the compound, as described herein, to an individual in need of such treatment or prophylaxis. Administration of the compound to a patient can agonize ObR activity to treat infertility by establishing a regular and/or increased program of voluntary food intake by the individual, thereby establishing a healthy physiological state in the individual.

Hypothalamic amenorrhea is a common cause of amenorrhea in women. Causes of hypothalamic amenorrhea include stress, weight loss (e.g., anorexia or bulimia), excessive exercise, certain medications, such as supplemental hormones, and hypothyroidism, among others. Accordingly, administration of an ObR agonist to such individuals, according to the present invention, can reinstate normal menstrual patterns by regulating leptin-mediated metabolism in these individuals.

The term "metabolic syndrome" is often used to refer to a cluster of adverse medical conditions including, but not limited to, insulin resistance without marked hyperglycemia, associated with atherosclerosis, obesity, hyperlipidemia, and essential hypertension. Treatments for metabolic syndrome include a reduction in voluntary food intake on the part of the affected individual. Therefore, the present invention includes a method of treating a patient having metabolic syndrome by administering an effective amount of a compound of the invention, or a pharmaceutical composition comprising the compound, as described herein, to the patient. Administration of a compound of the invention will induce satiety in the affected individual, and may enhance or recover attenuated sensitivity to leptin.

The presence of a leptin deficit in an individual can be readily detected in a patient by any means standard in the art, such as by measurement of systemic leptin levels by standard ELISA methods. The skilled artisan may be motivated to undertake such testing, for example, based on the nature of the disorder afflicting the patient (e.g., observation of obesity in obese patients and irregular menstruation in women with hypothalamic amenorrhea).

The amount of the therapeutic compound of the invention that will be effective in the treatment of a particular disorder or condition will depend on the nature of the disorder or condition, and is determined by standard clinical techniques. In addition, in vitro assays may optionally be employed to help identify optimal dosage ranges. The precise dose to be employed in the formulation also will depend on the route of administration and the seriousness of the disease, disorder, or condition and is decided according to the judgment of the practitioner and each patient's circumstances.

V. Administration of Compounds of the Invention

In an embodiment of the invention, the compounds are administered by way of a continuous-release transdermal patch. However, the compounds may be administered by any route, including oral, rectal, pulmonary, sublingual, and parenteral administration. Parenteral administration includes, for example, intravenous, intramuscular, intraarterial, intravesical (e.g., to the bladder), intradermal, transdermal, topical or subcutaneous administration.

Typically it is contemplated that treatment would be given at least once per day, typically once, twice, three times or four times per day with the doses given at equal intervals throughout the day and night in order to maintain a constant presence of the drug in order to induce sufficient agonistic activity in ObR. However, the skilled artisan will be aware that a treatment schedule can be optimized for any given patient, and that administration of compound may occur less frequently than once per day.

One or more compounds of the invention may be administered simultaneously, by the same or different routes, or at different times during treatment. The compounds of the invention may also be prescribed to be taken in combination with other drugs used to treat obesity, lipodystrophy, anorexia-mediated infertility, appetite control in obesity, metabolic syndrome, lipodystrophy-related infertility, diet-induced food craving, impaired cognitive functions and osteoporosis as a complication of hypothalamic amenorrhea. When used in such combinations compounds of the invention and conventional drugs may be administered simultaneously, by the same or different routes, or at different times during treatment. The dose of the conventional drug selected will depend on the particular compound being used and the route and frequency of administration.

The treatment may be carried out for as long a period as necessary. Typically it is contemplated that treatment would be continued indefinitely while the disease state persists, although discontinuation might be indicated if the compounds no longer produce a beneficial effect. The treating physician will know how to increase, decrease, or interrupt treatment based on patient response.

The specific dose of a compound according to the invention to obtain therapeutic benefit for treatment of a cellular proliferative disorder will, of course, be determined by the particular circumstances of the individual patient including the size, weight, age and sex of the patient, the nature and stage of the disease, the aggressiveness of the disease, and the route of administration of the compound.

For example, a daily dosage from about 0.02 to about 50 mg/kg/day may be utilized, more preferably from about 0.1 to about 10 mg/kg/day. Higher or lower doses are also contemplated as it may be necessary to use dosages outside these ranges in some cases. The daily dosage may be divided, such as being divided equally into two to four times per day daily dosing. Suitable dosage ranges for intravenous administration are generally about 20-500 micrograms of active compound per kilogram body weight.

The invention also provides a pharmaceutical pack or kit comprising one or more containers filled with one or more of the ingredients of the pharmaceutical compositions of the invention. Optionally associated with such container(s) is a notice in the form prescribed by a governmental agency regulating the manufacture, use or sale of pharmaceuticals or biological products, which notice reflects approval by the agency of manufacture, use or sale for human administration.

In accordance with the present invention, as described above or as discussed in the Examples below, there can be employed conventional clinical, chemical, cellular, histochemical, biochemical, molecular biology, microbiology and recombinant DNA techniques which are known to those of skill in the art. Such techniques are explained fully in the literature.

The invention should not be construed to be limited solely to the assays and methods described herein, but should be construed to include other methods and assays as well. One of skill in the art will know that other assays and methods are available to perform the procedures described herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

EXPERIMENTAL DESIGN AND METHODS

Peptide Design and Synthesis

The Site III region of leptin is known to bind to leptin receptors, and it is known that modification of select amino acid residues in this region may alter both the binding affinity and the biological activity of leptin. However, prior to the present invention, specific Site III leptin fragment agonists were not known.

The full-length amino acid sequence of human leptin is set forth in SEQ ID NO:1.

To test the agonistic (and potentially antagonistic) effects of isolated leptin domains, the following leptin Site III peptide fragments were synthesized in a manner in which the C-terminal carboxylic acid function was converted to an amide, —C(O)—NH$_2$. The amino acid sequences of Site III (leptin 117-132; SEQ ID NO:2) is: Ser-Gly-Tyr-Ser-Thr-Glu-Val-Val-Ala-Leu-Ser-Arg-Leu-Gln-Gly-Ser; and Site III Ala,Ala (leptin 117-132 with a double Alanine mutation) (SEQ ID NO:3) is: Ser-Gly-Tyr-Ala-Ala-Glu-Val-Val-Ala-Leu-Ser-Arg-Leu-Gln-Gly-Ser.

The leptin peptide fragments were prepared with a 5(6)-carboxy-fluorescein label at the amino terminus to examine molecular interactions. The sequences of the two peptides were extended to both termini relative to the published binding sites to ensure proper folding around the binding surfaces. Where possible, alpha helices were extended N-terminally up to the preceding turn in order to retain helix initiation even in the presence of an N-terminally attached fluorescein label.

Peptides were synthesized using solid-phase synthetic methods. The peptide chain assembly was conducted using either a CEM Liberty microwave-assisted automated synthesizer or a MultiSynTech SYRO multiple peptide synthesizer. TentaGel S-Ram-Fmoc resin was used with an initial load of 0.3 mmol/g (Advanced ChemTech). Standard Fmoc-chemistry was used throughout (G. B. Fields, et al., *Int. J. Pept. Protein Res.*, 1990, 35, 161-214), with a 4-molar excess of the acylating amino acids. The peptides were detached from the resin with the carboxyl function of the C-terminal residue being in the form of an amide, —C(O)—NH$_2$. Non-natural amino acids were coupled manually to ensure completion of synthesis.

Before cleavage, the resins were split into two equal parts, and one half of the resin was endcapped with 5(6)-carboxy fluorescein. Both unlabeled and labeled peptides were cleaved from the solid support with trifluoroacetic acid (TFA) in the presence of thioanisole (5%), and water (5%) as scavengers. After cleavage, the peptides were purified by RP-HPLC. Preparative RP-HPLC runs consisted of an isocratic elution of 5% acetonitrile in 0.1% TFA for 5 minutes followed by a linear gradient from 5% to 65% acetonitrile for 120 minutes. The final peptide products were characterized using RP-HPLC and MALDI-MS. The carbohydrate protecting acetyl groups were removed from the peptides using a 10 minute treatment with 0.01M NaOH, after which the reaction mixtures were immediately neutralized with an equal amount of 0.01M HCl. Mass spectra (PerSeptive Biosystems, Voyager DE instrument) identified correct (i.e., having the predicted molecular weight) and clean samples.

Biological Activity of the Peptide Candidates

For the evaluation of the biological activity of the synthesized leptin Site III peptide fragments, human cell lines were selected in which the ObR expression level is known. Two ObR-positive human cell models were used: MCF-7 breast cancer cells and DU-45 prostate cancer cells. Both cell lines express ObR, and leptin and leptin analogues stimulate their growth (C. Garofalo, et al., *Clin. Cancer Res.*, 2004, 10, 6466-6475; C. Garofalo, et al., *Clin. Cancer Res.*, 2006, 12, 1447-1453). Normal mammary epithelial MCF-10 cells lacking ObR were used as a negative control (X. Hu, et al., *J. Natl. Cancer Inst.*, 2002, 94, 1704-1711).

In order to test the stability of each of the Site III peptides in serum, 10 μL of an aqueous peptide stock solution containing about 0.8 mg/mL peptide was added to 200 μL 25% aqueous pooled mouse serum (M. F. Powell, et al., *Pharmacol. Res.*, 1993, 10, 1268-1273). The temperature of the peptide-serum mixture was maintained at 37° C. At 0 minutes, and after 45 minutes, 60 minutes, 90 minutes, 2 hours, 4 hours, and 8 hours, three samples of each peptide were taken, and precipitated by the addition of 40 μL 15% aqueous trichloroacetic acid. The samples were stored at 4° C. for 20 minutes, then subjected to centrifugation. The supernatants were immediately frozen on dry-ice and 220 μL of each was analyzed using. RP-HPLC and/or MALDI-MS.

Biological activity of the Site III peptides was assayed as follows. MCF-7 cells were stimulated with 6 nM full-sized leptin. The smaller leptin fragments and analogs were added to the cell culture at a concentration of 10 nM, 100 nM or 1 μM. Leptin at 10 nM concentration stimulated MCF-7 cell growth by approximately 40%, in line with previous observations (C. Garofalo, et al., *Clin. Cancer Res.*, 2004, 10, 6466-6475). All Site III peptides bound to the extracellular domain of ObR as documented by dot-blot or Western-blot analysis. The Site III Ala,Ala derivative antagonized leptin-induced cell proliferation in a concentration-dependent manner. The Site III Ala,Ala mutant peptide consistently exhibited a powerful leptin receptor antagonistic activity. In fact, it reversed leptin induced stimulation of MCF-7 cells at as low as 10 nM peptide concentration, with an additional 50% reduction in cell counts at 1 μM. When the assay was run at a more reliably measurable 1 μM peptide concentration, a consistent 6% decrease in cell numbers could be observed compared to the leptin only samples. In summary, in the presence of exogenously added full-sized leptin these assays verified the strong antagonist activity of the Site III Ala,Ala mutant.

The cell stimulation activity of the Site III peptides was assayed as follows. Human leptin was purchased from R&D Systems and used at a concentration of 100 ng/mL (approximately 6 nM). MCF-7 and DU-45 cells naturally expressing ObR were grown in a standard medium DMEM:F12 plus 5% fetal bovine serum. MCF-10 was grown in serum-free mammalian epithelial growth medium supplemented with 100 ng/mL cholera toxin. Seventy percent confluent cultures were synchronized in serum-free medium (DMEM plus 10 μM FeSO$_4$, plus 0.5% albumin) for 24 h and then treated with leptin and/or peptides (different doses) for 5 days. Cell counts before and after treatment were determined by counting the cells using trypan blue exclusion. All assays were conducted in triplicate and repeated at least twice.

It was also noted that the lack of exogenous leptin changes the mode as to how the antagonist peptides influence the growth of MCF-7 cells. When the Site III Ala,Ala analog was added to MCF-7 cells without leptin, it exhibited strong agonistic activity. Maximum cell stimulation for the Site III Ala, Ala derivative was observed at 1 μM peptide concentration. Pyrrhocoricin was selected as a negative control because it is equal in size with the leptin fragments, but with its Pro-Arg-Pro repeats, the sequence falls very far from the roughly neutral leptin analogs. The results on the other ObR expressing cancer cell line, DU-45 mirrored those obtained with MCF-7. The Site III Ala,Ala peptide was a medium-to-strong agonist. In the presence of leptin, the peptide showed moderate antagonist activity. The Site III peptide did not demonstrate a major effect on the proliferation of the control MCF-10 cell line. These data demonstrate that the assayed leptin fragments are partial agonists depending upon the presence of other ObR ligands during the assay conditions.

Comparison of Modified and Unmodified Peptide Fragment Activity

The leptin Site III peptide fragments showed variable mitogenic potential in MCF-7 cells. In the absence of full-length leptin, the Site III 117-132 fragment did not noticeably influence the cell growth in the 10 nM-1 µM concentration range. In the presence of 10 nM leptin, the same peptide showed minor antagonistic activity (21% reduction in leptin-induced cell growth at 1 µM) indicating that the partial agonist activities of the Site III Ala,Ala mutant were indeed due to the alanine substitutions. As further support, the site III fragment had no effect on the proliferation of either DU-45 or MCF-10 cells.

Experimental Example 1

Designer Site III Derivatives

Based on the results above, it appears that site III is the leptin region that can be further modified for obtaining peptide agonists. In designing peptide agonists, peptides of 12-13 residues were prepared, with hydrophobic residues placed at or near the peptide termini (to render the peptides more resistant to serum proteases). In two instances, full C-terminal blockade was attempted with acetylated diamino-propionic acid, a residue proven to increase peptide stability at the C-terminus without interfering in vivo or in vitro biological activities (L. Otvos, Jr., et al., *Protein Sci.*, 2000, 9, 742-749). Various specific amino acid residues were also replaced with unnatural analogs also to increase stability as well as to introduce full antagonistic or agonistic mutations. The modified residues included those that were shown to regulate peptide biological activity, such as Tyr119 and Ser120, as well as Glu122 and Ala125, two residues located at the one third and two third positions of the new 12-mer peptides. Tyr was replaced with the highly homologous Tyr(Me) or Tyr($I_2$), Glu was replaced with D-Gla (γ-carboxy-glutamic acid) and Ala was replaced with β-Ala or D-Ala. The serine was replaced with Ser-β(GlcAc$_4$), because a β-linked glucose moiety on serine was shown to promote the penetration of an enkephalin analog across the blood-brain barrier (R. Polt, et al., *Proc. Natl. Acad. Sci. USA*, 1994, 91, 7114-7118). The glycopeptide was tested both as acetylated and sugar side-chain deprotected (deacetylated) forms. The following peptides were synthesized:

F2:
(SEQ ID NO: 4)
Gly-Tyr($I_2$)-Ser-Thr-D-Gla-Val-Val-D-Ala-Leu-Ser-Arg-Leu

D12:
(SEQ ID NO: 5)
Tyr(Me)-Ser-Thr-D-Gla-Val-Val-D-Ala-Leu-Ser-Arg-Leu

A4:
(SEQ ID NO: 6)
Gly-Tyr($I_2$)-Ser-Thr-Glu-Val-Val-βAla-Leu-Ser-Arg-Leu

A11:
(SEQ ID NO: 7)
Tyr(Me)-Ser-Thr-Glu-Val-Val-βAla-Leu-Ser-Arg-Leu

E1Ac:
(SEQ ID NO: 8)
Tyr($I_2$)-Serβ(GlcAc$_4$)-Thr-Glu-Val-Val-Ala-Leu-Ser-Arg-Leu-Dap(Ac)

E1Free:
(SEQ ID NO: 9)
Tyr($I_2$)-Serβ(Glc)-Thr-Glu-Val-Val-Ala-Leu-Ser-Arg-Leu-Dap(Ac)

D6:
(SEQ ID NO: 10)
Gly-Tyr($I_2$)-Serβ(GlcAc$_4$)-Thr-Glu-Val-Val-Ala-Leu-Ser-Arg-Leu-Dap(Ac)

The results for the MALDI-MS analyses of the peptides is as follows:
F1: calculated 1589, found 1589;
D12: calculated 1294, found 1294;
A4 calculated 1545, found 1545;
A11: calculated 1250, found 1250;
E1Ac: calculated 1946, found 1947;
E1Free: calculated 1778, found 1779; and
D6: calculated 2003, found 2005.

ObR Agonist and Antagonist Activity of Designer Peptides

As with the Site III Ala,Ala derivative, the F2 and D12 peptides, featuring D-Gla and D-Ala replacements, were agonists to ObR expressed on MCF-7 cells in the absence of leptin, and antagonists in the presence of leptin (Table 1). F2 and D12, present at a 1 µM concentration without exogenous leptin present, stimulated the proliferation of MCF-7 cells by 120% and 37% respectively. When leptin was present, these peptides reversed leptin-induced cell stimulation by 15% and 43%. Apparently, the identity of the side-chain substituent on the tyrosine or the glycine amino extension had no influence on the in vitro biological activity.

The β-alanine-containing peptide A4 demonstrated almost identical activity on MCF-7 cells as its 13-mer variant F2 (Table 1). Similar to the D-Gla, D-Ala series, the shorter β-alanine-containing analog A11 was less agonistic in the absence of leptin than was the longer variant, although in the presence of leptin, A11 was basically inactive. Taken together, these site III analogs behaved very much like the combination of their unmodified Site III 117-132 and Site III Ala,Ala parent leptin fragments.

TABLE 1

| | Relative stimulation (%) of MCF-7 cells | |
|---|---|---|
| Peptide | No leptin added | With 10 nM leptin |
| F2 (SEQ ID NO. 4) | +120 | −15 |
| D12 (SEQ ID NO. 5) | +37 | −43 |
| A4 (SEQ ID NO. 6) | +102 | −10 |
| A11 (SEQ ID NO. 7) | +19 | −3 |

ObR Binding Activity of Designer Peptides

For dot-blot and ELISA assays, the leptin fragments were dissolved in electroblot transfer buffer (25 mM Tris and 192 M glycine buffer containing 20% methanol) and were applied to either a nitrocellulose membrane or dried upon ELISA plates (Otvos, L., Jr., and Szendrei, G. I. (1996) Enzyme-linked immunosorbent assay of peptides. In: *Neuropeptide*

Protocols (G. B. Irvine and C. H. Williams, eds.). Humana Press, Totowa, N.J., pp. 269-275). The solid surfaces were blocked with 5% BSA in a PBS-0.5% Tween 20 buffer (PBST) for 3 hours at room temperature and were subsequently incubated with 10 µg/mL solution of human IgG Fc-conjugated ObR extracellular domain (R&D Systems) dissolved in Tris-buffered saline-0.1% Tween 20 buffer (TBST) containing 1% bovine serum albumin (BSA) for 1 hour. A monoclonal goat antibody (Santa Cruz Biotechnology), specific for the N-terminus of human ObR, was added to the assay mixture, followed by addition of a horseradish peroxidase(HRP)-conjugated anti-goat IgG donkey antibody for the dot-blot assay, and HRP-conjugated anti-goat Fc mouse antibody for ELISA assay (used at a 1:15,000 dilution in PBST and 1% BSA). Between reagents, the solid surfaces were washed extensively with PBST. After washing with PBST, the membrane was treated with a chemiluminescence luminol oxidizer (NEN) for 1 min. The resultant chemiluminescence was exposed to a X-Omat blue XB-1 film (Kodak) for 10 seconds, and the exposed film was developed. The ELISA was developed using an HRP ELISA kit including tetramethylbenzidine as a substrate and sulfuric acid as a stop solution. Optical absorbance values were read at 490 nm using a microplate reader.

Both the E1Ac and E1Free peptides bound to the extracellular domain of ObR, as demonstrated using dot-blot and ELISA-type solid-phase binding assays in a dose-dependent manner FIG. 1A shows two results for the E1Ac peptide. The solid bars represent 20 µg peptide load and the shaded bars represent 10 µg of peptide dried to the assay plate. The negative control—the antibacterial peptide pyrrhocoricin—did not bind to ObR. The low solubility of the commercially available ObR extracellular fragment—human Fc chimera obfuscated the determination of accurate binding constants in solution.

Figure 1B:
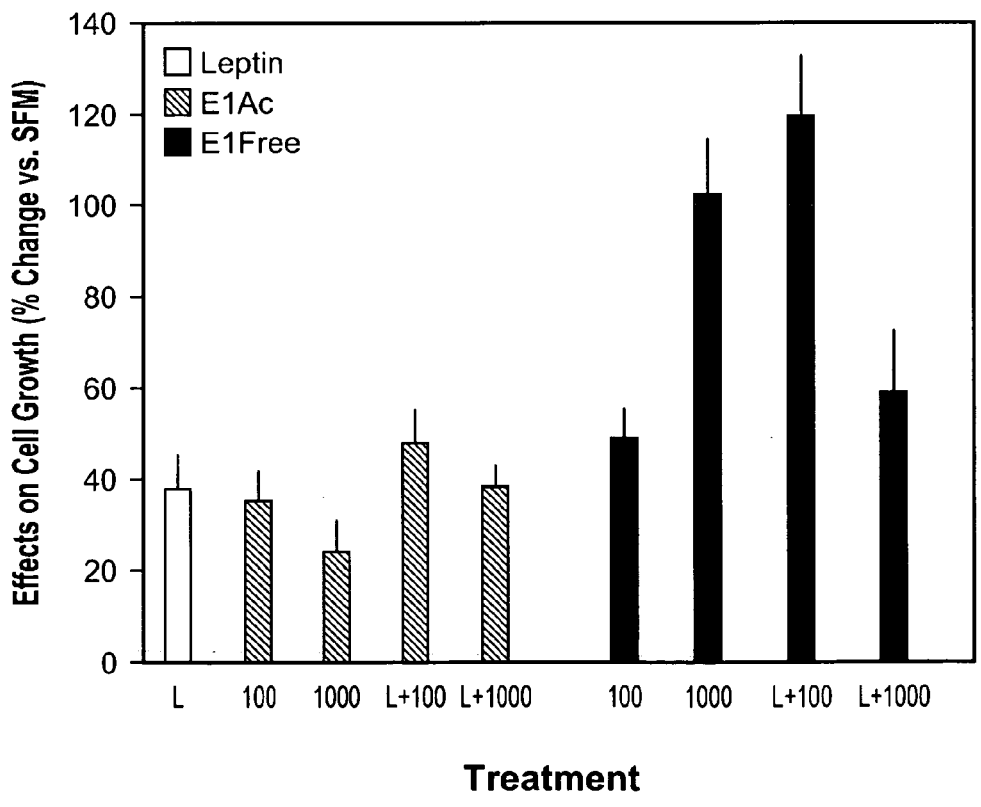

Similar to most site III peptide fragments and analogs, glycopeptides E1Ac and E1Free stimulated the proliferation of MCF-7 cells in a dose dependent manner (FIG. 1B). At 100 nM and 1000 nM concentrations, cell count increases of 54% and 101% (E1Ac) or 81% and 114% (E1Free) were observed, respectively. Nevertheless, as opposed to any other leptin fragment and analog set forth herein, neither E1 glycopeptide demonstrated any leptin antagonistic activity. In fact, at 1000 nM, both peptides further increased leptin-induced cell stimulation by 17% (E1Ac) and 84% (E1Free) (FIG. 1B). At the same concentrations used above, the E1Ac peptide was inactive with respect to MCF-10 normal mammary epithelial cells, within the experimental error of the assay. Peptides E1Ac and E1Free are full agonists to cells expressing ObR, demonstrating monofunctional, biological activity.

ObR Signaling Assays

To demonstrate that the MCF-7 and DU-45 cell stimulatory effects of the leptin peptides are due to activation of ObR, downstream signaling was monitored upon treatment of MCF-7 cells with E1Free peptide.

MCF-7 cells were grown and treated with E1Free peptide and full-sized leptin as described for the cell stimulation assays elsewhere herein. Cells were lysed with SDS sample buffer and scraped off of the plate. DNA was sheared using sonication, after which the sample was heated to 95° C., centrifuged and, subjected to SDS-PAGE. After gel electrophoresis, the proteins were transferred to nitrocellulose membrane. The membrane was incubated with 5% milk as blocking buffer, followed by addition of rabbit polyclonal antibodies to phosphorylated or total ERK1/2 MAP kinases (1:500 dilution in TBST and 2% milk, Cell Signaling Technology). The expression of a constitutive Hsp72/74 protein was probed with mouse monoclonal antibodies to control protein loading (1:5,000 dilution in TBST and 3% milk Calbiochem). After extensive washing, the blots incubated with HRP-conjugated secondary anti-rabbit (1:1,000 in TBST and 2% milk, Santa Cruz Biotechnology) and anti-mouse (1:10, 000 TBST and 3% milk, Amersham Biosciences) IgG antibodies produced in goats, and developed as described for the dot-blot above.

Figure 2:
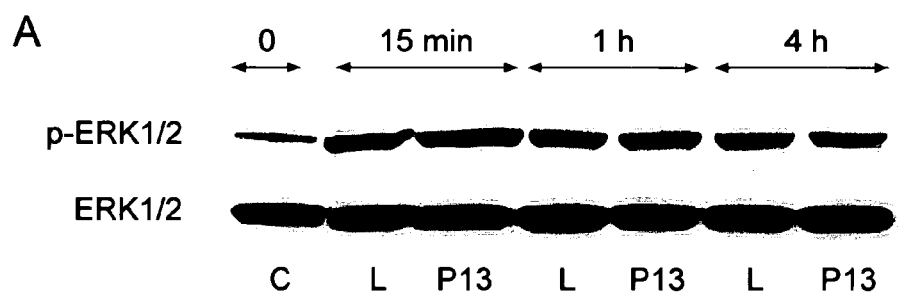
FIG. 2 is a series of images illustrating the effects of E1Free peptide (P13) on ERK 1/2 activation. Upper panel A of FIG. 2 illustrates the effect of either 6 nM leptin (L) or 100 nM E1Free peptide (P13) on MCF-7 cells synchronized in serum-free medium. The MCF-7 cells were contacted with peptide for 15 minutes, 1 hour or 4 hours. Lower panel B of FIG. 2 illustrates synchronized MCF-7 cells after treatment with 10-500 nM E1Free peptide (P13). The expression of phospho-ERK1/2 and total ERK1/2 was determined by Western blotting, using specific antibodies as described in the Experimental Examples below.
Figure 2:
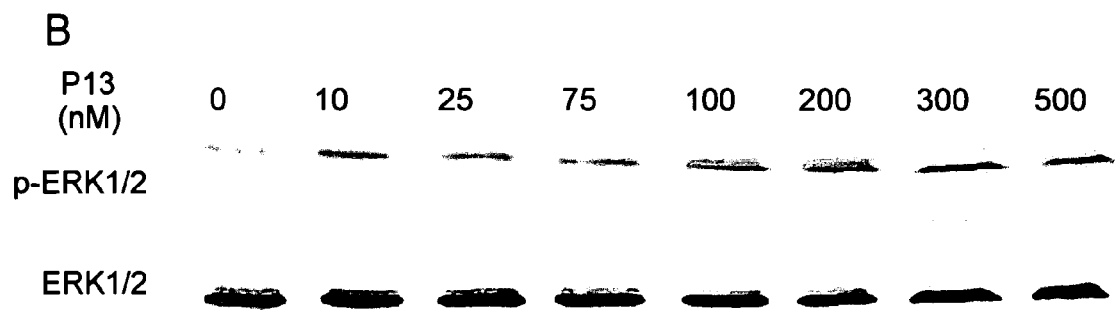

The results are shown in FIG. 2, where P13 (nM) indicates the concentration of E1Free peptide. Phosphorylation of ERK1/2 increased upon E1Free peptide addition, similar in degree and kinetics to the effects observed using full-sized leptin (FIG. 2), relative to phospho-ERK1/2. Steady measured amounts of total ERK1/2, indicated the specificity of ObR activation. An $EC_{50}$ value of approximately 100-150 nM was estimated for binding of the E1Free peptide to ObR, based on a maximum observed ERK1/2 stimulation by 200 nM E1Free.

Experimental Example 2

In Vitro Model of Blood-Brain-Barrier Penetration

To confirm the ability of the E1 peptides to cross the blood-brain barrier, penetration of the protected (E1Ac) and free (E1Free) glycopeptides across confluent layers of astrocytes, brain endothelial cells, or a double layer of these two cell types was examined, in comparison with the Site III Ala,Ala non-glycosylated analog. This cell model was shown to mimic the transport properties of drugs across the blood-brain barrier accurately (S. Lundquist, et al., *Pharm. Res.*, 2002, 19, 976-981).

A confluent monolayer of human astrocytes or brain capillary endothelial cells, or a dual layer of both cell types (astrocytes first, followed by endothelial cells) were grown at 37° C. on polycarbonate filters (Costar, Transwell, 0.4 µm) that were pretreated with collagen. Under these conditions, the endothelial cells retain the characteristics of the blood-brain-barrier, which include complex tight junctions, low rates of pinocytosis and low enzyme levels (S. Lundquist, et al., *Pharm. Res.*, 2002, 19, 976-981). A 0.1 mM solution of each of E1Ac, E1Free or Site III Ala,Ala was added to the upper compartment of the Transwell plates. The plates were then placed back in the incubator and samples were taken from the bottom compartments at 0, 5, 10, 30, and 120 minute intervals. The identity and quantity of peptides that had penetrated through the cell layers were subsequently analyzed by RP-HPLC and MALDI-MS.

All three peptides penetrate the cell layers, albeit with different efficacy. While the earliest time point at which the control non-glycosylated peptide could be detected was as late as 30 minutes, the glycopeptides were present in the bottom filter compartment as early as 10 minutes after addition. Although the presence of the sugar-protecting acetyl groups did not appear to modify the velocity of blood-brain barrier penetration, the acetyl groups may increase the amount of peptide traveling through in any given time period.

Experimental Example 3

In Vivo Biodistribution of E1Free Peptide

E1Free peptide was co-synthesized with the near-infrared absorbing fluorescent dye DY675 and the resultant labeled peptide was purified by RP-HPLC. Forty microgams of the peptide was injected intraperiotoneally into shaved and isoflurane anesthesized female Balb/c mice. For imaging of the biodistribution of the peptide, the animals were placed into a fluorescence microscope chamber under continuous isoflurane exposure. Fluorescence exposure pictures were taken with an IVIS microscope set to a 695 nm emission wavelength. Images were obtained once a minute for the first ten minutes after peptide addition and every five minutes afterwards, until a 65 minute stop point was reached.

Figure 3:
FIG. 3 is an image illustrating the biodistribution of E1Free peptide labeled with the DY675 stain at its N-terminus.
Figure 4:
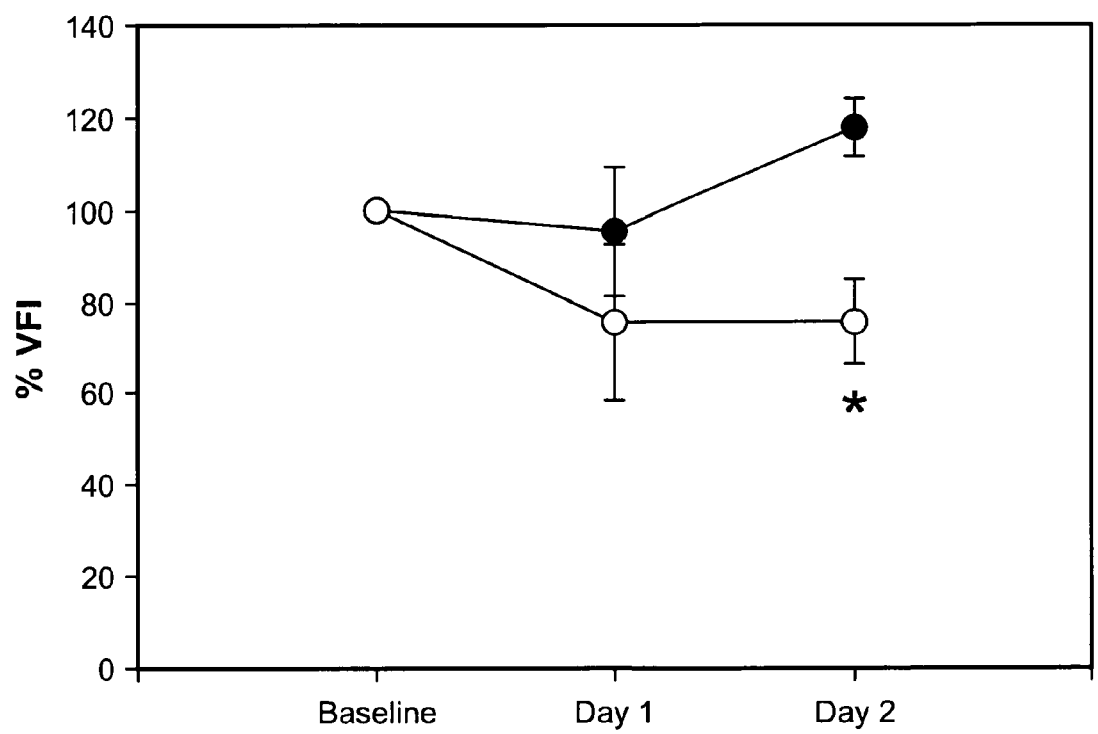
FIG. 4 is an image illustrating the effect of leptin agonist peptide E1Free administered at 10 μg/hour for 7 hours, on food intake (n=4) in program-fed animals (food available 1100-1600 hours). Voluntary food intake was reduced by approx. 25% in E1Free-treated animals (open circles) compared to controls (aCSF: closed circles, *P<0.05).

FIG. 3 illustrates the biodistribution of the E1Free peptide, and shows that the peptide localizes in the head, as well as the kidneys and liver. This result suggests that peptide crosses the blood-brain barrier, and can therefore successfully reach the brain for effective targeting of the leptin receptor.

Experimental Example 4

Voluntary Food Intake in Animals Treated with E1Free Peptide

The fact that elevated levels of circulating leptin do not cause satiety in obese individuals is one demonstration of the phenomenon of leptin resistance. This attenuation in the ability of leptin to regulate food intake may arise for various reasons, such as a reduced transport of leptin across the blood brain barrier. This attenuation may also arise due to leptin resistance—or reduced efficacy of leptin—to activate and initiate the signal transduction pathways required to induce satiety.

This experiment was conducted using ovariectomised (OVX) ewes (n=4/group: 55 kg). Ovariectomy removes cyclic effects of ovarian steroids, which affect sensitivity to leptin. The experiments were performed in an isolated room with an ambient temperature range of 17-22° C. E1Free peptide was administered to animals by way of Silastic cannulae introduced into the lateral cerebral ventricle (H8) for intracerebroventricular (icv) infusion. For infusion, pyrogen-free leptin peptide was dissolved in 0.1 mM HCl and diluted in artificial cerebrospinal fluid (aCSF) to a concentration of 10 μg/100 μl. All infusions were initiated at 0900 hours and control animals received an infusion of aCSF 100 μl/hour.

The results shown in FIG. 4 illustrate that animals receiving E1Free peptide voluntarily reduce the amount of food taken in over the course of two days. This result demonstrates that the E1Free peptide induces satiety, and can be used for appetite control.

Experimental Example 5

Additional Designer Site III Derivatives

Following the same procedures as described in Experimental Example 1, above, the following peptides are also synthesized.

DiMeTyr:
(SEQ ID NO: 11)
Tyr($Me_2$)-Ser(Glc)-Thr-Glu-Val-Val-Ala-Leu-Ser-Arg-Leu-Dap(Ac)

Ser(Gal):
(SEQ ID NO: 12)
Tyr($I_2$)-Ser(GalNAc)-Thr-Glu-Val-Val-Ala-Leu-Ser-Arg-Leu-Dap(Ac)

Thr(Gal):
(SEQ ID NO: 13)
Tyr($I_2$)-Ser-Thr(GalNAc)-Glu-Val-Val-Ala-Leu-Ser-Arg-Leu-Dap(Ac)

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A compound of the formula:

X-Glu-Val-Val-Ala-Leu-Y-Arg-Leu-Z      (SEQ ID NO:14)

wherein:
(a) X is selected from the group consisting of
    (i) zero amino acids,
    (ii) a hydroxyamino acid,
    (iii) a saccharide-modified hydroxyamino acid,
    (iv) $X_1$-$X_2$, wherein $X_1$ is a hydroxyamino acid, a saccharide-modified hydroxyamino acid or Asn, and $X_2$ is a hydroxyamino acid, a saccharide-modified hydroxyamino acid or Asn; and
    (v) $X_3$-$X_4$-$X_5$, wherein $X_3$ is a non-natural amino acid or an acetylated amino acid, $X_4$ is a hydroxyamino acid, a saccharide-modified hydroxyamino acid or Asn, and $X_5$ is a hydroxyamino acid, a saccharide-modified hydroxyamino acid or Asn,
(b) Y is a hydroxyamino acid, a saccharide-modified hydroxyamino acid or Asn, and
(c) Z is selected from the group consisting of
    (i) a non-natural amino acid which resists exopeptidase activity in a mammal, and
    (ii) $Z_1$-$Z_2$, wherein $Z_1$ is a single natural or non-natural amino acid and $Z_2$ is a single natural or non-natural amino acid which resists exopeptidase activity in a mammal,
wherein the C-terminal carboxyl group is optionally derivatized as an ester or an amide, or a salt thereof.

2. The compound of claim 1, or a salt thereof, wherein
(a) X is $X_3$-$X_4$-$X_5$, wherein $X_4$ is serine with a GlcAc$_4$ residue covalently O-linked to said serine through a beta-linkage,
(b) Y is serine, and
(c) Z is Dap(Ac).

3. The compound of claim 1, or a salt thereof, wherein
(a) X is $X_3$-$X_4$-$X_5$, wherein $X_4$ is serine with a Glc residue covalently O-linked to said serine through a beta-linkage,
(b) Y is serine, and
(c) Z is Dap(Ac).

4. The compound of claim 1, or a salt thereof, wherein X is $X_3$-$X_4$-$X_5$, wherein $X_4$ and $X_5$ are independently selected from the group consisting of serine, threonine, homoserine, hydroxypiperidine carboxylic acid, a saccharide-modified serine, a saccharide-modified threonine, a saccharide-modified homoserine, and a saccharide-modified hydroxypiperidine carboxylic acid.

5. The compound of claim 4, or a salt thereof, further wherein $X_4$ is a saccharide-modified serine wherein the saccharide moiety is selected from the group consisting of a monosaccharide, a disaccharide, and a trisaccharide moiety.

6. The compound of claim 5, or a salt thereof, wherein said saccharide moiety is selected from the group consisting of β(GlcAc4), α(GlcAc4), Man, Gal, Glc, GalNAc, GlcNAc, and combinations thereof.

7. The compound of claim 1, or a salt thereof, wherein X is $X_3$-$X_4$-$X_5$ and $X_3$ is selected from the group consisting of diiodotyrosine, bromotyrosine, nitrotyrosine, methyltyrosine, phosphotyrosine, or sulfotyrosine.

8. The compound of claim 1, or a salt thereof, wherein Y is serine, threonine, homoserine, hydroxypiperidine carboxylic acid, a saccharide-modified serine, a saccharide-modified threonine, a saccharide-modified homoserine, or a saccharide-modified hydroxypiperidine carboxylic acid.

9. The compound of claim 1, or a salt thereof, wherein Z is selected from the group consisting of Dap(Ac), diaminobutyric acid, norleucine, and norvaline.

10. The compound of claim 1 or a salt thereof, wherein Z is $Z_1$-$Z_2$, wherein $Z_1$ is leucine and $Z_2$ is Dap(Ac).

11. The compound of claim 6, or a salt thereof, wherein
(a) $X_3$ is 3,5-diiodotyrosine,
(b) $X_4$ is serine with a GlcAc$_4$ residue covalently O-linked to said serine through a beta-linkage,
(c) $X_5$ is threonine,
(d) Y is serine, and
(e) Z is Dap(Ac),
wherein the C-terminal carboxyl group is optionally derivatized as an ester or an amide.

12. The compound of claim 6, or a salt thereof, wherein
(a) $X_3$ is 3,5-diiodotyrosine,
(b) $X_4$ is serine with a Glc residue covalently O-linked to said serine through a beta-linkage,
(c) $X_5$ is threonine,
(d) Y is serine, and
(e) Z is Dap(Ac),
wherein the C-terminal carboxyl group is optionally derivatized as an ester or an amide.

13. A compound of the formula:

A-X-Glu-Val-Val-Ala-Leu-Y-Arg-Leu-Z where X-Glu-Val-Val-Ala-Leu-Y-Arg-Leu-Z is SEQ ID NO: 46 and
wherein:
(a) X is selected from the group consisting of
    (i) zero amino acids,
    (ii) a hydroxyamino acid,
    (iii) a saccharide-modified hydroxyamino acid, (iv) $X_1$-$X_2$, wherein $X_1$ is a hydroxyamino acid, a saccharide-modified hydroxyamino acid or Asn and $X_2$ is a hydroxyamino acid, a saccharide-modified hydroxyamino acid or Asn; and (v) $X_3$-$X_4$-$X_5$, wherein $X_3$ is a non-natural amino acid or an acetylated amino acid, $X_4$ is a hydroxyamino acid, a saccharide-modified hydroxyamino acid or Asn, and $X_5$ is a hydroxyamino acid, a saccharide-modified hydroxyamino acid or Asn, (b) Y is a hydroxyamino acid, a saccharide-modified hydroxyamino acid or Asn, (c) Z is a single natural or non-natural amino acid which resists exopeptidase activity in a mammal, and (d) A is a peptide transduction domain covalently attached to the N-terminal amino acid residue of said compound;

wherein the C-terminal carboxyl group is optionally derivatized to an ester or an amide, or a salt thereof.

14. A compound of the formula:

X-Glu-Val-Val-Ala-Leu-Y-Arg-Leu-Z-B where X-Glu-Val-Val-Ala-Leu-Y-Arg-Leu-Z is SEQ ID NO: 47, and wherein:

(a) X is selected from the group consisting of (i) zero amino acids, (ii) a hydroxyamino acid, (iii) a saccharide-modified hydroxyamino acid, (iv) $X_1$-$X_2$, wherein $X_1$ is a hydroxyamino acid, a saccharide-modified hydroxyamino acid or Asn and $X_2$ is a hydroxyamino acid, a saccharide-modified hydroxyamino acid or Asn; and (v) $X_3$-$X_4$-$X_5$, wherein $X_3$ is a non-natural amino acid or an acetylated amino acid, $X_4$ is a hydroxyamino acid, a saccharide-modified hydroxyamino acid or Asn, and $X_5$ is a hydroxyamino acid, a saccharide-modified hydroxyamino acid or Asn, (b) Y is a hydroxyamino acid, a saccharide-modified hydroxyamino acid or Asn, (c) Z is a single natural or non-natural amino acid which resists exopeptidase activity in a mammal, and (d) B is a peptide transduction domain covalently attached to Z; or a salt thereof.

15. The compound of claim 13, wherein the peptide transduction domain is polycationic.

16. The compound of claim 14, wherein the peptide transduction domain is polycationic.

17. A compound of the formula:

X-Glu-Val-Val-Ala-Leu-Y-Arg-Leu-Z (SEQ ID NO: 14), or a salt thereof, wherein:

(a) X is $X_3$-$X_4$-$X_5$, wherein $X_3$ is a non-natural amino acid or an acetylated amino acid, and $X_4$ and $X_5$ are independently selected from the group consisting of serine, threonine, homoserine, hydroxypiperidine carboxylic acid, a saccharide-modified serine, a saccharide-modified threonine, a saccharide-modified homoserine, and a saccharide-modified hydroxypiperidine carboxylic acid, (b) Y is a hydroxyamino acid, a saccharide-modified hydroxyamino acid or Asn, and (c) Z is selected from the group consisting of (i) a non-natural amino acid which resists exopeptidase activity in a mammal, and (ii) $Z_1$-$Z_2$, wherein $Z_1$ is a natural or non-natural amino acid and $Z_2$ is a natural or non-natural amino acid which resists exopeptidase activity in a mammal, wherein the C-terminal carboxyl group is optionally derivatized as an ester or an amide, or a salt thereof.

18. The compound of claim 17, or a salt thereof, further wherein $X_4$ is a saccharide-modified serine wherein the saccharide moiety is selected from the group consisting of a monosaccharide, a disaccharide, and a trisaccharide moiety.

19. The compound of claim 17, or a salt thereof, wherein said saccharide moiety is selected from the group consisting of β(GlcAc4), α(GlcAc4), Man, Gal, Glc, GalNAc, GlcNAc, and combinations thereof.

20. A compound of the formula:

X-Glu-Val-Val-Ala-Leu-Y-Arg-Leu-Z (SEQ ID NO: 14), or a salt thereof, wherein:

(a) X is $X_3$-$X_4$-$X_5$ and $X_3$ is selected from the group consisting of diiodotyrosine, bromotyrosine, nitrotyrosine, methyltyrosine, phosphotyrosine, or sulfotyrosine, $X_4$ is a hydroxyamino acid, a saccharide-modified hydroxyamino acid or Asn, and $X_5$ is a hydroxyamino acid, a saccharide-modified hydroxyamino acid or Asn, (b) Y is a hydroxyamino acid, a saccharide-modified hydroxyamino acid or Asn, and (c) Z is selected from the group consisting of (i) a non-natural amino acid which resists exopeptidase activity in a mammal, and (ii) $Z_1$-$Z_2$, wherein $Z_1$ is a natural or non-natural amino acid and $Z_2$ is a natural or non-natural amino acid which resists exopeptidase activity in a mammal, wherein the C-terminal carboxyl group is optionally derivatized as an ester or an amide, or a salt thereof.

21. A pharmaceutical composition comprising at least one compound of claim 1, 13, 14, 17 or 20, or a salt thereof, and a pharmaceutically-acceptable carrier.

22. A method of treating lipodystrophy in a subject in need of such treatment, said method comprising administering to said subject an effective amount of the compound of claim 1, 13, 14, 17 or 20, or a salt thereof.

23. A method of treating infertility in a subject in need of such treatment, said method comprising administering to said subject an effective amount of the compound of claim 1, 13, 14, 17 or 20, or a salt thereof, wherein said infertility is selected from the group consisting of anorexia-related infertility, lipodystrophy-related infertility, and infertility associated with polycystic ovarian syndrome.

24. A method of treating obesity in a subject in need of such treatment, said method comprising administering to said subject an effective amount of the compound of claim 1, 13, 14, 17 or 20, or a salt thereof.

25. A method of treating metabolic syndrome in a subject in need of such treatment, said method comprising administering to said subject an effective amount of the compound of claim 1, 13, 14, 17 or 20, or a salt thereof.

26. A method of treating hypothalamic amenorrhea in a subject in need of such treatment, said method comprising administering to said subject an effective amount of the compound of claim 1, 13, 14, 17 or 20, or a salt thereof.

* * * * *

SEQUENCE LISTING

```
<160> NUMBER OF SEQ ID NOS: 47

<210> SEQ ID NO 1
<211> LENGTH: 167
<212> TYPE: PRT
<213> ORGANISM: Homo sapiens

<400> SEQUENCE: 1

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

Thr Leu Ile Lys Thr Ile Val Thr Arg Ile Asn Asp Ile Ser His Thr
        35                  40                  45

Gln Ser Val Ser Ser Lys Gln Lys Val Thr Gly Leu Asp Phe Ile Pro
    50                  55                  60

Gly Leu His Pro Ile Leu Thr Leu Ser Lys Met Asp Gln Thr Leu Ala
65                  70                  75                  80

Val Tyr Gln Gln Ile Leu Thr Ser Met Pro Ser Arg Asn Val Ile Gln
                85                  90                  95
```

```
Ile Ser Asn Asp Leu Glu Asn Leu Arg Asp Leu Leu His Val Leu Ala
                100                 105                 110

Phe Ser Lys Ser Cys His Leu Pro Trp Ala Ser Gly Leu Glu Thr Leu
            115                 120                 125

Asp Ser Leu Gly Gly Val Leu Glu Ala Ser Gly Tyr Ser Thr Glu Val
        130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 2
<211> LENGTH: 16
<212> TYPE: PRT
<213> ORGANISM: Artificial Sequence
<220> FEATURE:
<223> OTHER INFORMATION: Chemically artificially synthesized

<400> SEQUENCE: 2

Ser Gly Tyr Ser Thr Glu Val Val Ala Leu Ser Arg Leu Gln Gly Ser
1               5                   10                  15

<210> SEQ ID NO 3
<211> LENGTH: 16
<212> TYPE: PRT
<213> ORGANISM: Artificial Sequence
<220> FEATURE:
<223> OTHER INFORMATION: Chemically artificially synthesized

<400> SEQUENCE: 3

Ser Gly Tyr Ala Ala Glu Val Val Ala Leu Ser Arg Leu Gln Gly Ser
1               5                   10                  15

<210> SEQ ID NO 4
<211> LENGTH: 12
<212> TYPE: PRT
<213> ORGANISM: Artificial Sequence
<220> FEATURE:
<223> OTHER INFORMATION: Chemically artificially synthesized
<220> FEATURE:
<221> NAME/KEY: MOD_RES
<222> LOCATION: (2)..(2)
<223> OTHER INFORMATION: diiodotyrosine
<220> FEATURE:
<221> NAME/KEY: MOD_RES
<222> LOCATION: (5)..(5)
<223> OTHER INFORMATION: D-Gla
<220> FEATURE:
<221> NAME/KEY: MOD_RES
<222> LOCATION: (8)..(8)
<223> OTHER INFORMATION: D-Ala

<400> SEQUENCE: 4

Gly Xaa Ser Thr Xaa Val Val Xaa Leu Ser Arg Leu
1               5                   10

<210> SEQ ID NO 5
<211> LENGTH: 11
<212> TYPE: PRT
<213> ORGANISM: Artificial Sequence
<220> FEATURE:
<223> OTHER INFORMATION: Chemically artificially synthesized
<220> FEATURE:
<221> NAME/KEY: MOD_RES
<222> LOCATION: (1)..(1)
<223> OTHER INFORMATION: methyltyrosine
<220> FEATURE:
<221> NAME/KEY: MOD_RES
<222> LOCATION: (4)..(4)
```

```
<223> OTHER INFORMATION: D-Gla
<220> FEATURE:
<221> NAME/KEY: MOD_RES
<222> LOCATION: (7)..(7)
<223> OTHER INFORMATION: D-Ala

<400> SEQUENCE: 5

Xaa Ser Thr Xaa Val Val Xaa Leu Ser Arg Leu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Chemically artificially synthesized
<220> FEATURE:
<221> NAME/KEY: MOD_RES
<222> LOCATION: (2)..(2)
<223> OTHER INFORMATION: diiodotyrosine
<220> FEATURE:
<221> NAME/KEY: MOD_RES
<222> LOCATION: (8)..(8)
<223> OTHER INFORMATION: bAla

<400> SEQUENCE: 6

Gly Xaa Ser Thr Glu Val Val Xaa Leu Ser Arg Leu
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Chemically artificially synthesized
<220> FEATURE:
<221> NAME/KEY: MOD_RES
<222> LOCATION: (1)..(1)
<223> OTHER INFORMATION: methyltyrosine
<220> FEATURE:
<221> NAME/KEY: MOD_RES
<222> LOCATION: (7)..(7)
<223> OTHER INFORMATION: bAla

<400> SEQUENCE: 7

Xaa Ser Thr Glu Val Val Xaa Leu Ser Arg Leu
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Chemically artificially synthesized
<220> FEATURE:
<221> NAME/KEY: MOD_RES
<222> LOCATION: (1)..(1)
<223> OTHER INFORMATION: diiodotyrosine
<220> FEATURE:
<221> NAME/KEY: MOD_RES
<222> LOCATION: (2)..(2)
<223> OTHER INFORMATION: [2,3,4,6-O-acetyl-beta-D-glucosyl] Serine
<220> FEATURE:
<221> NAME/KEY: MOD_RES
<222> LOCATION: (12)..(12)
<223> OTHER INFORMATION: N2(3)-acetyl-diaminopropionic acid

<400> SEQUENCE: 8

Xaa Xaa Thr Glu Val Val Ala Leu Ser Arg Leu Xaa
1               5                   10

<210> SEQ ID NO 9
```

<211> LENGTH: 12
<212> TYPE: PRT
<213> ORGANISM: Artificial Sequence
<220> FEATURE:
<223> OTHER INFORMATION: Chemically artificially synthesized
<220> FEATURE:
<221> NAME/KEY: MOD_RES
<222> LOCATION: (1)..(1)
<223> OTHER INFORMATION: diiodotyrosine
<220> FEATURE:
<221> NAME/KEY: MOD_RES
<222> LOCATION: (2)..(2)
<223> OTHER INFORMATION: beta glucosyl Serine
<220> FEATURE:
<221> NAME/KEY: MOD_RES
<222> LOCATION: (12)..(12)
<223> OTHER INFORMATION: N2(3)-acetyl-diaminopropionic acid

<400> SEQUENCE: 9

Xaa Xaa Thr Glu Val Val Ala Leu Ser Arg Leu Xaa
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Chemically artificially synthesized
<220> FEATURE:
<221> NAME/KEY: MOD_RES
<222> LOCATION: (2)..(2)
<223> OTHER INFORMATION: diiodotyrosine
<220> FEATURE:
<221> NAME/KEY: MOD_RES
<222> LOCATION: (3)..(3)
<223> OTHER INFORMATION: [2,3,4,6-O-acetyl-beta-D-glucosyl] Serine
<220> FEATURE:
<221> NAME/KEY: MOD_RES
<222> LOCATION: (13)..(13)
<223> OTHER INFORMATION: N2(3)-acetyl-diaminopropionic acid

<400> SEQUENCE: 10

Gly Xaa Xaa Thr Glu Val Val Ala Leu Ser Arg Leu Xaa
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Chemically artificially synthesized
<220> FEATURE:
<221> NAME/KEY: MOD_RES
<222> LOCATION: (1)..(1)
<223> OTHER INFORMATION: dimethyltyrosine
<220> FEATURE:
<221> NAME/KEY: MOD_RES
<222> LOCATION: (2)..(2)
<223> OTHER INFORMATION: Glucosyl Serine
<220> FEATURE:
<221> NAME/KEY: MOD_RES
<222> LOCATION: (12)..(12)
<223> OTHER INFORMATION: N2(3)-acetyl-diaminopropionic acid

<400> SEQUENCE: 11

Xaa Xaa Thr Glu Val Val Ala Leu Ser Arg Leu Xaa
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Chemically artificially synthesized

```
<220> FEATURE:
<221> NAME/KEY: MOD_RES
<222> LOCATION: (1)..(1)
<223> OTHER INFORMATION: diiodotyrosine
<220> FEATURE:
<221> NAME/KEY: MOD_RES
<222> LOCATION: (2)..(2)
<223> OTHER INFORMATION: [N-acetyl galactosamyl] Serine
<220> FEATURE:
<221> NAME/KEY: MOD_RES
<222> LOCATION: (12)..(12)
<223> OTHER INFORMATION: N2(3)-acetyl-diaminopropionic acid

<400> SEQUENCE: 12

Xaa Xaa Thr Glu Val Val Ala Leu Ser Arg Leu Xaa
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Chemically artificially synthesized
<220> FEATURE:
<221> NAME/KEY: MOD_RES
<222> LOCATION: (1)..(1)
<223> OTHER INFORMATION: diiodotyrosine
<220> FEATURE:
<221> NAME/KEY: MOD_RES
<222> LOCATION: (3)..(3)
<223> OTHER INFORMATION: [N-acetyl galactosamyl] Threonine
<220> FEATURE:
<221> NAME/KEY: MOD_RES
<222> LOCATION: (12)..(12)
<223> OTHER INFORMATION: N2(3)-acetyl-diaminopropionic acid

<400> SEQUENCE: 13

Xaa Ser Xaa Glu Val Val Ala Leu Ser Arg Leu Xaa
1               5                   10

<210> SEQ ID NO 14
<211> LENGTH: 13
<212> TYPE: PRT
<213> ORGANISM: Artificial Sequence
<220> FEATURE:
<223> OTHER INFORMATION: Chemically artificially synthesized
<220> FEATURE:
<221> NAME/KEY: VARIANT
<222> LOCATION: (1)..(1)
<223> OTHER INFORMATION: is a non-natural amino acid or acetylated amino
      acid when residues 2 and 3 are present, or is absent whenever
      residue 2 is absent
<220> FEATURE:
<221> NAME/KEY: VARIANT
<222> LOCATION: (2)..(2)
<223> OTHER INFORMATION: is a hydroxyamino acid, a saccharide-modified
      hydroxyamino acid, or Asn when residue 3 is present, or is absent
      whenever residue 3 is absent
<220> FEATURE:
<221> NAME/KEY: VARIANT
<222> LOCATION: (3)..(3)
<223> OTHER INFORMATION: is a hydroxyamino acid, a saccharide-modified
      hydroxyamino acid, or Asn when residue 2 is present, is a
      hydroxyamino acid or a saccharide-modified hydroxyamino acid when
      residue 2 is absent, or is absent
<220> FEATURE:
<221> NAME/KEY: VARIANT
<222> LOCATION: (9)..(9)
<223> OTHER INFORMATION: is a hydroxyamino acid, a saccharide-modified
      hydroxyamino acid or Asn
<220> FEATURE:
<221> NAME/KEY: VARIANT
<222> LOCATION: (12)..(12)
<223> OTHER INFORMATION: is a natural or non-natural amino acid when
      residue 13 is present, or, when residue 13 is absent, is a
      non-natural amino acid which resists exopeptidase activity in a
```

-continued

```
      mammal & the C-term. -COOH is optionally derivatized as an ester
      or an amide
<220> FEATURE:
<221> NAME/KEY: VARIANT
<222> LOCATION: (13)..(13)
<223> OTHER INFORMATION: is, when present, a natural or non-natural
      amino acid which resists exopeptidase activity in a mammal & the
      C-term. -COOH is optionally derivatized as an ester or an amide,
      or is absent

<400> SEQUENCE: 14

Xaa Xaa Xaa Glu Val Val Ala Leu Xaa Arg Leu Xaa Xaa
1               5                   10

<210> SEQ ID NO 15
<211> LENGTH: 12
<212> TYPE: PRT
<213> ORGANISM: Human immunodeficiency virus

<400> SEQUENCE: 15

Tyr Gly Arg Lys Lys Arg Arg Gln Arg Arg Gly
1               5                   10

<210> SEQ ID NO 16
<211> LENGTH: 14
<212> TYPE: PRT
<213> ORGANISM: Human immunodeficiency virus

<400> SEQUENCE: 16

Gly Arg Lys Lys Arg Arg Gln Arg Arg Arg Pro Pro Gln Cys
1               5                   10

<210> SEQ ID NO 17
<211> LENGTH: 13
<212> TYPE: PRT
<213> ORGANISM: Human immunodeficiency virus

<400> SEQUENCE: 17

Gly Arg Lys Lys Arg Arg Gln Arg Arg Arg Pro Pro Gln
1               5                   10

<210> SEQ ID NO 18
<211> LENGTH: 11
<212> TYPE: PRT
<213> ORGANISM: Human immunodeficiency virus

<400> SEQUENCE: 18

Tyr Gly Arg Lys Lys Arg Arg Gln Arg Arg
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic sequence based on HIV TAT

<400> SEQUENCE: 19

Tyr Ala Arg Lys Ala Arg Arg Gln Ala Arg Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic sequence based on HIV TAT
```

```
<400> SEQUENCE: 20

Tyr Ala Arg Ala Ala Ala Arg Gln Ala Arg Ala
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic sequence based on HIV TAT

<400> SEQUENCE: 21

Tyr Ala Arg Ala Ala Arg Arg Ala Ala Arg Arg
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic sequence based on HIV TAT

<400> SEQUENCE: 22

Tyr Ala Arg Ala Ala Arg Arg Ala Ala Arg Ala
1               5                   10

<210> SEQ ID NO 23
<211> LENGTH: 16
<212> TYPE: PRT
<213> ORGANISM: Drosophila melanogaster

<400> SEQUENCE: 23

Arg Gln Ile Lys Ile Trp Phe Gln Asn Arg Arg Met Lys Trp Lys Lys
1               5                   10                  15

<210> SEQ ID NO 24
<211> LENGTH: 16
<212> TYPE: PRT
<213> ORGANISM: Artificial Sequence
<220> FEATURE:
<223> OTHER INFORMATION: Reverse Sequence of pAntp (43-48)

<400> SEQUENCE: 24

Lys Lys Trp Lys Met Arg Arg Asn Gln Phe Trp Val Lys Val Gln Arg
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: W/R Penetratin

<400> SEQUENCE: 25

Arg Arg Trp Arg Arg Trp Trp Arg Arg Trp Trp Arg Arg Trp Arg Arg
1               5                   10                  15

<210> SEQ ID NO 26
<211> LENGTH: 7
<212> TYPE: PRT
<213> ORGANISM: Drosophila melanogaster

<400> SEQUENCE: 26

Arg Arg Met Lys Trp Lys Lys
1               5
```

<210> SEQ ID NO 27
<211> LENGTH: 7
<212> TYPE: PRT
<213> ORGANISM: Artificial Sequence
<220> FEATURE:
<223> OTHER INFORMATION: Arginine 7-mer

<400> SEQUENCE: 27

Arg Arg Arg Arg Arg Arg Arg
1               5

<210> SEQ ID NO 28
<211> LENGTH: 9
<212> TYPE: PRT
<213> ORGANISM: Artificial Sequence
<220> FEATURE:
<223> OTHER INFORMATION: Arginine 9-mer

<400> SEQUENCE: 28

Arg Arg Arg Arg Arg Arg Arg Arg Arg
1               5

<210> SEQ ID NO 29
<211> LENGTH: 30
<212> TYPE: PRT
<213> ORGANISM: herpes simplex virus 1

<400> SEQUENCE: 29

Asp Ala Ala Thr Arg Ser Ala Ala Ser Arg Pro Thr Glu Arg Pro Arg
1               5                   10                  15

Ala Pro Ala Arg Ser Ala Ser Arg Pro Arg Arg Pro Val Glu
            20                  25                  30

<210> SEQ ID NO 30
<211> LENGTH: 16
<212> TYPE: PRT
<213> ORGANISM: Human immunodeficiency virus

<400> SEQUENCE: 30

Gly Ala Leu Phe Leu Gly Trp Leu Gly Ala Ala Gly Ser Thr Met Gly
1               5                   10                  15

<210> SEQ ID NO 31
<211> LENGTH: 27
<212> TYPE: PRT
<213> ORGANISM: Human immunodeficiency virus

<400> SEQUENCE: 31

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val
            20                  25

<210> SEQ ID NO 32
<211> LENGTH: 27
<212> TYPE: PRT
<213> ORGANISM: Artificial Sequence
<220> FEATURE:
<223> OTHER INFORMATION: Caiman crocodylus Ig(v) light chain- SN40NLS

<400> SEQUENCE: 32

Met Gly Leu Gly Leu His Leu Leu Val Leu Ala Ala Ala Leu Gln Gly
1               5                   10                  15

Ala Trp Ser Gln Pro Lys Lys Lys Arg Lys Val
            20                  25

-continued

```
<210> SEQ ID NO 33
<211> LENGTH: 12
<212> TYPE: PRT
<213> ORGANISM: Hepatitis B virus

<400> SEQUENCE: 33

Pro Leu Ser Ser Ile Phe Ser Arg Ile Gly Asp Pro
1               5                   10

<210> SEQ ID NO 34
<211> LENGTH: 12
<212> TYPE: PRT
<213> ORGANISM: Hepatitis B virus

<400> SEQUENCE: 34

Phe Trp Arg Gly Asp Leu Val Phe Asp Phe Gln Val
1               5                   10

<210> SEQ ID NO 35
<211> LENGTH: 25
<212> TYPE: PRT
<213> ORGANISM: Vesicular stomatitis virus

<400> SEQUENCE: 35

Lys Phe Thr Ile Val Phe Pro His Asn Gln Lys Gly Asn Trp Lys Asn
1               5                   10                  15

Val Pro Ser Asn Tyr His Tyr Cys Pro
            20                  25

<210> SEQ ID NO 36
<211> LENGTH: 20
<212> TYPE: PRT
<213> ORGANISM: Adenovirus

<400> SEQUENCE: 36

Ala Lys Arg Ala Arg Leu Ser Thr Ser Phe Asn Pro Val Tyr Pro Tyr
1               5                   10                  15

Glu Asp Glu Ser
            20

<210> SEQ ID NO 37
<211> LENGTH: 27
<212> TYPE: PRT
<213> ORGANISM: Artificial Sequence
<220> FEATURE:
<223> OTHER INFORMATION: Ttansportan

<400> SEQUENCE: 37

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 38
<211> LENGTH: 18
<212> TYPE: PRT
<213> ORGANISM: Artificial Sequence
<220> FEATURE:
<223> OTHER INFORMATION: SynB1

<400> SEQUENCE: 38

Arg Gly Gly Arg Leu Ser Tyr Ser Arg Arg Arg Phe Ser Thr Ser Thr
1               5                   10                  15

Gly Arg
```

```
<210> SEQ ID NO 39
<211> LENGTH: 16
<212> TYPE: PRT
<213> ORGANISM: Kaposi's sarcoma-associated herpesvirus

<400> SEQUENCE: 39

Ala Ala Val Ala Leu Leu Pro Ala Val Leu Leu Ala Leu Leu Ala Pro
1               5                   10                  15

<210> SEQ ID NO 40
<211> LENGTH: 12
<212> TYPE: PRT
<213> ORGANISM: Kaposi's sarcoma-associated herpesvirus

<400> SEQUENCE: 40

Ala Ala Val Leu Leu Pro Val Leu Leu Ala Ala Pro
1               5                   10

<210> SEQ ID NO 41
<211> LENGTH: 15
<212> TYPE: PRT
<213> ORGANISM: Homo sapiens

<400> SEQUENCE: 41

Val Thr Val Leu Ala Leu Gly Ala Leu Ala Gly Val Gly Val Gly
1               5                   10                  15

<210> SEQ ID NO 42
<211> LENGTH: 30
<212> TYPE: PRT
<213> ORGANISM: Artificial Sequence
<220> FEATURE:
<223> OTHER INFORMATION: P3 membrane fusion sequence

<400> SEQUENCE: 42

Val Ala Tyr Ile Ser Arg Gly Gly Val Ser Thr Tyr Tyr Ser Asp Thr
1               5                   10                  15

Val Lys Gly Arg Phe Thr Arg Gln Lys Tyr Asn Lys Arg Ala
            20                  25                  30

<210> SEQ ID NO 43
<211> LENGTH: 18
<212> TYPE: PRT
<213> ORGANISM: Artificial Sequence
<220> FEATURE:
<223> OTHER INFORMATION: Model ambiphilic peptide

<400> SEQUENCE: 43

Lys Leu Ala Leu Lys Leu Ala Leu Lys Ala Leu Lys Ala Ala Leu Lys
1               5                   10                  15

Leu Ala

<210> SEQ ID NO 44
<211> LENGTH: 30
<212> TYPE: PRT
<213> ORGANISM: Artificial Sequence
<220> FEATURE:
<223> OTHER INFORMATION: Model ambiphilic peptide

<400> SEQUENCE: 44

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30
```

```
<210> SEQ ID NO 45
<211> LENGTH: 12
<212> TYPE: PRT
<213> ORGANISM: Artificial Sequence
<220> FEATURE:
<223> OTHER INFORMATION: Synthetic protein transduction domain

<400> SEQUENCE: 45

Arg Arg Gln Arg Arg Thr Ser Lys Leu Met Lys Arg
1               5                   10

<210> SEQ ID NO 46
<211> LENGTH: 12
<212> TYPE: PRT
<213> ORGANISM: Artificial Sequence
<220> FEATURE:
<223> OTHER INFORMATION: Chemically artificially synthesized
<220> FEATURE:
<221> NAME/KEY: VARIANT
<222> LOCATION: (1)..(1)
<223> OTHER INFORMATION: is a non-natural amino acid or acetylated amino
      acid when residues 2 and 3 are present, or is absent whenever
      residue 2 is absent
<220> FEATURE:
<221> NAME/KEY: VARIANT
<222> LOCATION: (2)..(2)
<223> OTHER INFORMATION: is a hydroxyamino acid, a saccharide-modified
      hydroxyamino acid, or Asn when residue 3 is present, or is absent
      whenever residue 3 is absent
<220> FEATURE:
<221> NAME/KEY: VARIANT
<222> LOCATION: (3)..(3)
<223> OTHER INFORMATION: is a hydroxyamino acid, a saccharide-modified
      hydroxyamino acid, or Asn when residue 2 is present,is a
      hydroxyamino acid or a saccharide-modified hydroxyamino acid when
      residue 2 is absent, or is absent
<220> FEATURE:
<221> NAME/KEY: VARIANT
<222> LOCATION: (9)..(9)
<223> OTHER INFORMATION: is a hydroxyamino acid, a saccharide-modified
      hydroxyamino acid, or Asn
<220> FEATURE:
<221> NAME/KEY: VARIANT
<222> LOCATION: (12)..(12)
<223> OTHER INFORMATION: is a natural or non-natural amino acid which
      resists exopeptidase activity in a mammal & the C-term. -COOH is
      optionally derivatized as an ester or an amide

<400> SEQUENCE: 46

Xaa Xaa Xaa Glu Val Val Ala Leu Xaa Arg Leu Xaa
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Chemically artificially synthesized
<220> FEATURE:
<221> NAME/KEY: VARIANT
<222> LOCATION: (1)..(1)
<223> OTHER INFORMATION: is a non-natural amino acid or acetylated amino
      acid when residues 2 and 3 are present, or is absent whenever
      residue 2 is absent
<220> FEATURE:
<221> NAME/KEY: VARIANT
<222> LOCATION: (2)..(2)
<223> OTHER INFORMATION: is a hydroxyamino acid, a saccharide-modified
      hydroxyamino acid, or Asn when residue 3 is present, or is absent
      whenever residue 3 is absent
<220> FEATURE:
<221> NAME/KEY: VARIANT
<222> LOCATION: (3)..(3)
<223> OTHER INFORMATION: is a hydroxyamino acid, a saccharide-modified
```

```
        hydroxyamino acid, or Asn when residue 2 is present, is a
        hydroxyamino acid or a saccharide-modified hydroxyamino acid when
        residue 2 is absent, or is absent
<220> FEATURE:
<221> NAME/KEY: VARIANT
<222> LOCATION: (9)..(9)
<223> OTHER INFORMATION: is a hydroxyamino acid, a saccharide-modified
        hydroxyamino acid, or Asn
<220> FEATURE:
<221> NAME/KEY: VARIANT
<222> LOCATION: (12)..(12)
<223> OTHER INFORMATION: is a natural or non-natural amino acid which
        resists exopeptidase activity in a mammal

<400> SEQUENCE: 47

Xaa Xaa Xaa Glu Val Val Ala Leu Xaa Arg Leu Xaa
1               5                   10
```